(12) United States Patent
Broberg et al.

(10) Patent No.: US 10,471,043 B2
(45) Date of Patent: Nov. 12, 2019

(54) COMPOUNDS AND METHODS OF TREATING BACTERIAL INFECTIONS

(71) Applicant: ULTUPHARMA AB, Uppsala (SE)

(72) Inventors: Anders Broberg, Uppsala (SE); Pierre Andersson, Uppsala (SE); Jolanta Levenfors, Orbyhus (SE); Joakim Bjerketorp, Uppsala (SE); Christer Sahlberg, Nacka (SE)

(73) Assignee: Ultupharma AB, Uppsala (SE)

( * ) Notice: Subject to any disclaimer, the term of this patent is extended or adjusted under 35 U.S.C. 154(b) by 0 days.

(21) Appl. No.: 15/780,419

(22) PCT Filed: Dec. 2, 2016

(86) PCT No.: PCT/SE2016/051207
§ 371 (c)(1),
(2) Date: May 31, 2018

(87) PCT Pub. No.: WO2017/095319
PCT Pub. Date: Jun. 8, 2017

(65) Prior Publication Data
US 2018/0360802 A1 Dec. 20, 2018

(30) Foreign Application Priority Data
Dec. 2, 2015 (SE) .................................... 1551572

(51) Int. Cl.
*C07D 309/38* (2006.01)
*A61K 31/366* (2006.01)
*C07D 309/30* (2006.01)
*C07D 309/32* (2006.01)
*A61K 31/351* (2006.01)
*A61P 31/04* (2006.01)

(52) U.S. Cl.
CPC .......... *A61K 31/366* (2013.01); *A61K 31/351* (2013.01); *A61P 31/04* (2018.01); *C07D 309/30* (2013.01); *C07D 309/32* (2013.01)

(58) Field of Classification Search
CPC .................................................... C07D 309/38
USPC ....................................................... 549/292
See application file for complete search history.

(56) References Cited

FOREIGN PATENT DOCUMENTS

| JP | 2003040711 A | 2/2003 |
|---|---|---|
| JP | 2013095719 A | 5/2013 |
| WO | 9514012 A1 | 5/1995 |
| WO | 200814311 A2 | 1/2008 |

OTHER PUBLICATIONS

Tabuchi, H., 'Modification of the Fries type rearrangement of the 0-enol acyl group using N,N-dicyclohexylcarbodiimide and 4-dimethylaminopyridine'. Synlett 1993, vol. 9, pp. 651-652.
Bouaziz, O., Reactivite de l'acide dehydroacetique hydrogene en C5-C6 : obtention des pyrano-1,5-benzodiazepines differemment substituees et de la structure enaminone. Comptes Rendus Chimie 2012, vol. 15, No. 9, pp. 774-778.
Trost, B. M., 'Ruthenium-Catalyzed Alder Ene Type Reactions. A Formal Synthesis of Alternaric Acid'. Journal of the American Chemical Society 1998, vol. 120, No. 36, pp. 9228-9236.
Lokot, I. P.. 'Synthesis of 3-acyl(alkyl)-6-methylpyran-2,4-diones and their derivatives'. Russian Journal of Organic Chemistry (Translation of Zhurnal Organicheskoi Khimii) 1999, vol. 35, No. 5, pp. 746-755.
Ichimoto, I., 'Stereoselective synthesis of podoblantins and their antiblast activity'. J. Pesticide Sci, vol. 13, No. 4, pp. 605-613, 1998.
Carneiro, V. M. T. et al., 'Is RK-682 a promiscuous enzyme inhibitor? Synthesis and in vitro evaluation of protein tyrosine phosphatase inhibition of racemic RK-682 and analogues'. European Journal of Medicinal Chemistry 2015, vol. 97, pp. 42-54.
Sato, K., et al., "The Oxidation of 2,3-Dihydro-4H-pyran-4-ones", Bulletin of the Chemical Society of Japan, vol. 46, 1973, pp. 1288-1290.
International Search Report cited in PCT/SE2016/051207, dated Feb. 20, 2017, 6 pages.

*Primary Examiner* — Niloofar Rahmani
(74) *Attorney, Agent, or Firm* — Rothwell, Figg, Ernst & Manbeck, P.C.

(57) ABSTRACT

The invention relates to compounds of Formula (I), wherein the variables are as defined in the claims, which are useful in the treatment and/or prevention of bacterial infections in a subject. The invention further relates to the use of a compound of Formula (I) in the manufacture of a medicament, and medical devices when used in a method of treating or preventing a bacterial infection in a subject, and related aspects.

Formula (I)

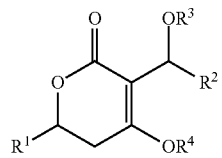

29 Claims, No Drawings

COMPOUNDS AND METHODS OF TREATING BACTERIAL INFECTIONS

CROSS REFERENCE TO RELATED APPLICATION

This application is a 35 U.S.C. 371 National Phase Entry Application from PCT/SE2016/051207, filed Dec. 2, 2016, which claims the benefit of Swedish Patent Application No. 1551572-9 filed on Dec. 2, 2015, the disclosure of which is incorporated herein in its entirety by reference.

TECHNICAL FIELD

This invention relates to compounds of Formula I, methods of treating, eliminating and/or preventing a bacterial infection in a subject using a compound of Formula I, the use of a compound of Formula I in the manufacture of a medicament for the treatment of a bacterial infection in a subject, and medical devices when used in a method of treating or preventing a bacterial infection in a subject.

BACKGROUND ART

A marked increase in prevalence of multi-drug resistance in disease-causing Gram-positive G+ve (inter alia *Staphylococcus aureus, Enterococcus* spp., *Streptococcus pneumoniae, Clostridium difficile, Mycobacterium tuberculosis*) and Gram-negative bacteria (inter alia *Klebsiella* spp., *Neisseria gonorrhoeae, Acinetobacter* spp., *Campylobacter* spp., *Enterobacter* spp., *Pseudomonas aeruginosa, Salmonella* spp., *Shigella* spp.) has coincided with an unprecedented global decline in investment in new anti-infective drugs. There are few currently registered alternatives for multidrug resistant (MDR) bacterial infections, forcing clinicians to consider older generation drugs such as colistin with narrow spectrum and considerable potential for toxic side-effects. In addition, there are fewer novel classes of anti-infective therapeutics moving through the drug development pipeline.

Since the year 2000, a period of almost 15 years, only 5 novel mode of action (MOA) antibacterial agents have been approved by the US FDA—linezolid (an oxazolidinone) in 2000, daptomycin (a lipopeptide) in 2003, retapamulin (a pleuromutilin) in 2007, fidaxomicin (a macrolide tiacumicin) in 2011, and bedaquiline (a diarylquinoline) in 2012. No novel MOA antibacterial agents were approved in 2013 and to date in 2014 only tedizolid and dalbavancin, both analogues of existing classes, have been recommended for approval in the US. While there are more than 300 anti-infective medicines in various stages of development, the large majority of these medicines are previously approved antibacterial compounds or their derivatives that are undergoing studies for new indications.

Furthermore, the prevalence of multidrug-resistance in animal-specific pathogens together with greater regulation of the registration and usage of antimicrobials in animals, has caused veterinarians to become increasingly reliant on the traditional classes of antimicrobial agents. The risk of transfer of MDR zoonotic organisms from animals to humans has also led to calls for further restrictions on the usage of some recently registered antibacterial drugs such as the fluoroquinolones and the third and fourth generation cephalosporins.

Epidemiology of Antibacterial Resistance Development in Pathogens of Humans and Animals Much of the evolution in resistance development is driven by changes in the epidemiology of key MDR organisms. Once only restricted to human hospitals and aged care facilities, methicillin resistant *Staphylococcus aureus* (MRSA) strains are now being isolated from the community in alarming proportions. Furthermore, community-acquired MRSA strains are more likely to carry the Panton-Valentine leukocidin (PVL) toxin, a virulence factor linked to skin and soft tissue lesions as well as a rapid, fulminating, necrotizing pneumonia with significant associated mortality. Recently MRSA strains have become host-adapted in several key animal species including livestock, horses and companion animals and regular cases of human-to-animal and animal-to-human transfer are being documented. This has important consequences for strain transmission and public health. A recent survey of 751 Australian veterinarians for MRSA nasal carriage found that a remarkable 21.4% of equine veterinarians were MRSA-positive compared to 4.9% of small animal veterinarians and 0.9% of veterinarians with little animal contact. These ecological shifts of MRSA together with the emergence of resistance to new drugs developed specifically for MRSA such as linezolid, confirm that new MRSA anti-infectives are urgently needed. Furthermore, hospitals that use vancomycin for treating MRSA then have to contend with outbreaks of vancomycin-resistant enterococci (VRE) infections in their patients, once again with limited alternative antimicrobial choices.

The World Health Organisation has identified antibiotic resistance as one of the three major future threats to global health. A recent report from the US Centers for Disease Control and Prevention (CDC) estimated that "in the United States, more than two million people are sickened every year with antibiotic-resistant infections, with at least 23,000 dying as a result." The extra medical costs, in the USA alone, associated with treating and managing a single case of antibiotic-resistant infection are estimated to be between US$18,588 and US$29,069 per year resulting in an overall direct cost to the US health system of over US$20 billion annually. In addition, the cost to US households in terms of lost productivity is estimated at over US$35 billion per annum. Twenty five thousand patients in the European Union (EU) still die annually from infection with MDR bacteria despite many EU countries having world's best practice hospital surveillance and infection control strategies. The EU costs from health care expenses and lost productivity associated with MDR infections are estimated to be at least €1.5 billion per year.

There is an unmet clinical need for antibacterial agents with novel mechanisms of action to supplement and replace currently available antibacterial agents, the efficacy of which is increasingly undermined by antibacterial resistance mechanisms. There additionally remains a need for alternative antibacterials in the treatment of infection by multi-resistant bacteria. However, as reported by the Infectious Diseases Society of America and the European Centre for Disease Control and Prevention, few new drugs are being developed that offer promising results over existing treatments (Infectious Diseases Society of America 2010, Clinical Infectious Diseases, 50(8): 1081-1083).

Ayer W A & Villar J D F Can J Chem 63, 1161 (1985) describe an enolic natural product isolated from the fungus *Lachnellula fuscosanguinea*, which they term lachnellulic acid:

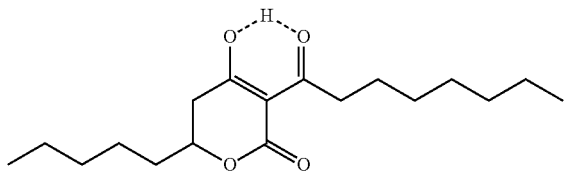

The compound is active against the Dutch Elm disease fungus. Note that the alkyl chain adjacent the enolic keto function is longer than the chain adjacent the lactone.

Kong et al, J. Nat. Prod. 2005 68, 920-923 describe natural products isolated from a *Pseudomonas* species associated with a Pacific marine sponge, which they term pseudopyronines A & B:

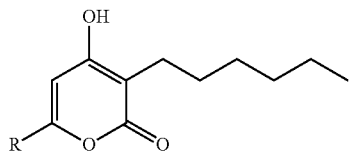

Pseudopyronine A: R = (CH$_2$)$_3$CH$_3$
Pseudopyronine B: R = (CH$_2$)$_5$CH$_3$ The compounds are described as having "moderate to poor" antibacterial activities, but are unstable and degrade to a hydroxyfuranone species. Note that the pyranone ring has two unsaturated bonds. In a related paper, Singh et al J Antibiotics 56 No 12 1033-1044 (2003), the antibacterial activity of the compounds is believed to derive from inhibition of the bacterial fatty acid biosynthesis pathway, in a somewhat similar fashion to the antibacterial agent triclosan.

Miyakado et al Chem Lett 10 1539-42 (1982) describes the isolation of natural products from the plant *Podophyllum peltatum*, which they term podoblastin A:

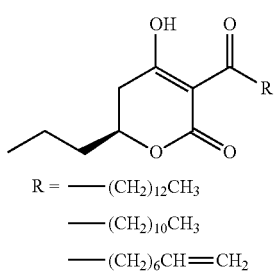

R = ——(CH$_2$)$_{12}$CH$_3$
——(CH$_2$)$_{10}$CH$_3$
——(CH$_2$)$_6$CH═CH$_2$

The compounds are said to be active against the fungus *Pyricularia oryziae*. Note that the alkyl chain adjacent the carbonyl is markedly longer than the alkyl chain adjacent the lactone.

The discussion of the background art set out above is intended to facilitate an understanding of the present invention only. The discussion is not an acknowledgement or admission that any of the material referred to is or was part of the common general knowledge as at the priority date of the application.

SUMMARY OF INVENTION

According to one aspect of the invention, there is provided a compound of Formula I, or a stereoisomer, tautomer, pharmaceutically acceptable salt, or prodrug thereof:

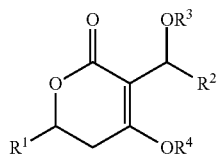

Formula I wherein
$R^1$ is $C_1$-$C_{20}$alkyl, $C_2$-$C_{20}$alkenyl, $C_2$-$C_{20}$alkynyl, $C_1$-$C_6$alkoxy$C_1$-$C_3$alkyl or $C_3$-$C_6$ cycloalkyl$C_1$-$C_3$alkyl, in which any alkyl, alkenyl, alkynyl or cycloalkyl is optionally substituted with up to three substituents independently selected from halo, —OR$_5$, —C(O)OR$^5$, —C(O)R$^5$, —OC(O)OR$^5$, —NR$^5$R$^6$, —C(O)NR$^5$R$^6$, —OC(O)NR$^5$R$^6$, nitro, cyano and azido, and in the case of cycloalkyl, also $C_1$-$C_6$alkyl or $C_1$-$C_6$haloalkyl;
$R^2$ is $C_1$-$C_{20}$alkyl, $C_2$-$C_{20}$alkenyl, $C_2$-$C_{20}$alkynyl, $C_1$-$C_6$alkoxy$C_1$-$C_3$alkyl, $C_1$-$C_6$ cycloalkyl$C_1$-$C_3$alkyl or $C_1$-$C_6$cyloalkenyl$C_1$-$C_3$alkyl, in which any alkyl, alkenyl, alkynyl, cycloalkyl or cycloalkenyl is optionally substituted with up to three substituents independently selected from halo, —OR$^5$, —C(O)OR$^5$, —C(O)R$^5$, —OC(O)OR$^5$, —NR$^5$R$^6$, —C(O)NR$^5$R$^6$, —OC(O)NR$^5$R$^6$, nitro, cyano and azido, and in the case of cycloalkyl, also $C_1$-$C_6$alkyl or $C_1$-$C_6$haloalkyl;
$R^3$ is a bond along with the adjacent carbon defining a keto group, $R^5$, C(O)R$^5$, CR$^a$R$^b$OR$^5$, CR$^a$R$^b$OC(O)R$^5$, CR$^a$R$^b$O-C(O)OR$^5$ or C(O)CHR$^7$NH$_2$;
$R^4$ is R$^5$, C(O)R$^5$, CR$^a$R$^b$OR$^5$, CR$^a$R$^b$OC(O)R$^5$, CR$^a$R$^b$OC(O)OR$^5$ or C(O)CHR$^7$RNH$_2$;
$R^5$ and $R^6$ are independently selected from H, $C_1$-$C_6$alkyl, $C_3$-$C_6$cycloalkyl and $C_3$-$C_6$cycloalkyl$C_1$-$C_3$alkyl, wherein the $C_1$-$C_6$alkyl or cycloalkyl is optionally substituted with halo, hydroxy, $C_1$-$C_4$alkoxy, $C_1$-$C_4$haloalkyl, hydroxy$C_1$-$C_4$alkyl, $C_1$-$C_4$alkylcarbonyl, SH, SMe, COOH, COOC$_1$-$C_4$alkyl and CONH$_2$;
$R^7$ is H, $C_1$-$C_6$alkyl, $C_3$-$C_6$cycloalkyl and $C_3$-$C_6$cycloalkyl$C_1$-$C_3$alkyl, wherein the $C_1$-$C_6$alkyl or $C_3$-$C_6$cycloalkyl is optionally substituted with halo, hydroxy, phenyl, $C_1$-$C_4$alkoxy, $C_1$-$C_4$haloalkyl, hydroxy$C_1$-$C_4$alkyl, $C_1$-$C_4$alkylcarbonyl, SH, SMe, COOH, COOC$_1$-$C_4$alkyl and CONH$_2$;
$R^a$ and $R^b$ are independently selected from H and methyl;
or a pharmaceutically acceptable salt, stereoisomer, N-oxide or hydrate thereof; with the proviso that when $R^3$ is a bond, $R^4$ is H, and $R^1$ and $R^2$ are both unsubstituted alkyl, then if $R^1$ is $C_6$-alkyl, $R^2$ has at least two carbon atoms.

In certain embodiments, $R^1$ is $C_1$-$C_{20}$alkyl which is optionally substituted as defined above. In sub-embodiments, $R^1$ is $C_6$-$C_{12}$alkyl, including n-hexyl, n-heptyl, n-octyl, n-decyl, n-undecyl and n-dodecyl, especially n-nonyl, any of which alkyl species being optionally substituted with 1, 2 or 3 substituents independently selected from $C_1$-$C_4$alkyl, $C_1$-$C_4$haloalkyl, halo, hydroxy, $C_1$-$C_4$alkoxy, $C_1$-$C_4$hydroxyalkyl and $C_1$-$C_4$alkylcarbonyl.

Further, $R^1$ may be selected from the group consisting of $C_2$-$C_{20}$alkyl; $C_3$-$C_{20}$alkyl; $C_4$-$C_{20}$alkyl; $C_5$-$C_{20}$alkyl; $C_6$-$C_{20}$alkyl; $C_7$-$C_{20}$alkyl; and $C_8$-$C_{20}$alkyl. In this embodiment, $R^2$ may be selected from the group consisting of $C_2$-$C_{19}$alkyl; $C_2$-$C_{18}$alkyl; $C_2$-$C_{17}$alkyl; $C_2$-$C_{16}$alkyl; $C_2$-$C_{15}$alkyl; $C_2$-$C_{14}$alkyl; and $C_2$-$C_{13}$alkyl. Thus, advantageously, a shorter $R^1$ substituent may be combined in Formula I with a longer $R^2$ substituent, whether it is alkyl, alkenyl or alkynyl. The herein defined ranges for $R^1$ and $R^2$ may be combined with anyone of the herein defined other R substituents.

In certain embodiments $R^1$ is $C_2$-$C_{20}$alkenyl comprising one to three unsaturated bonds which is optionally substituted as defined above. In sub-embodiments, $R^1$ is $C_6$-$C_{12}$alkenyl, such as hexenyl, heptenyl, octenyl, decenyl, undecenyl or dodecenyl, including those with one unsaturated bond, and especially those in the 1-position.

The bond connecting $R^1$ to the pyran ring is chiral, and the invention includes certain embodiments which are racemic at this position, or embodiments enantiomerically enriched with the S or R diastereomer, for example 75% enantiomerically enriched as regards one diastereomer, typically greater than 90% enantiomerically enriched, such as greater than 95% enantiomerically enriched.

In certain embodiments, $R^2$ is $C_1$-$C_{20}$alkyl which is optionally substituted as defined above. In sub-embodiments, $R^1$ is $C_1$-$C_6$alkyl, including methyl, ethyl, n-propyl, isopropyl, n-butyl, isobutyl, sec-butyl, tert-butyl, n-pentyl and n-hexyl, any of which alkyl species being optionally substituted with 1, 2 or where valance permits 3 substituents independently selected from $C_1$-$C_4$ alkyl, $C_1$-$C_4$ haloalkyl, halo, hydroxy, $C_1$-$C_4$alkoxy, $C_1$-$C_4$hydroxyalkyl and $C_1$-$C_4$alkylcarbonyl.

In certain embodiments, $R^2$ is $C_1$-$C_6$cycloalkyl$C_1$-$C_3$alkyl which is optionally substituted as defined above. Subembodiments include cyclopropylmethyl, cyclobutylmethyl, cyclopentylmethyl and especially cycloehexylmethyl, any of which cycloalkyl species being optionally substituted with 1, 2 or where valance permits 3 substituents independently selected from $C_1$-$C_4$alkyl, $C_1$-$C_4$haloalkyl, halo, hydroxy, $C_1$-$C_4$alkoxy, $C_1$-$C_4$hydroxyalkyl and $C_1$-$C_4$alkylcarbonyl.

An additional proviso may be applied to Formula I, wherein when $R^3$ is a bond, $R^4$ is H, and $R^1$ and $R^2$ are both unsubstituted $C_1$-$C_{20}$ alkyl, then $R^1$ has at least 2 more carbon atoms than $R^2$.

In an advantageous embodiment, $R^2$ is a $C_3$alkyl, combined with any one of the herein discussed other substituents following the defined proviso(s).

The compound according to the invention may be selected from the group consisting of:
3-butyryl-4-hydroxy-6-nonyl-5,6-dihydro-2H-pyran-2-one,
(R)-3-butyryl-4-hydroxy-6-nonyl-5,6-dihydro-2H-pyran-2-one,
(S)-3-butyryl-4-hydroxy-6-nonyl-5,6-dihydro-2H-pyran-2-one,
6-decyl-4-hydroxy-3-pentanoyl-5,6-dihydro-2H-pyran-2-one,
(E)-3-butyryl-6-(non-1-en-1-yl)-4-hydroxy-5,6-dihydro-2H-pyran-2-one,
4-hydroxy-6-nonyl-3-propionyl-5,6-dihydro-2H-pyran-2-one,
4-hydroxy-6-octyl-3-propionyl-5,6-dihydro-2H-pyran-2-one,
3-acetyl-4-hydroxy-6-octyl-5,6-dihydro-2H-pyran-2-one,
4-hydroxy-6-nonyl-3-pentanoyl-5,6-dihydro-2H-pyran-2-one,
3-acetyl-4-hydroxy-6-nonyl-5,6-dihydro-2H-pyran-2-one,
6-decyl-4-hydroxy-3-propionyl-5,6-dihydro-2H-pyran-2-one,
3-acetyl-6-decyl-4-hydroxy-5,6-dihydro-2H-pyran-2-one,
3-butyryl-6-decyl-4-hydroxy-5,6-dihydro-2H-pyran-2-one,
3-butyryl-4-hydroxy-6-octyl-5,6-dihydro-2H-pyran-2-one,
3-(2-cyclohexylacetyl)-4-hydroxy-6-nonyl-5,6-dihydro-2H-pyran-2-one,
4-hydroxy-3-(3-methylbutanoyl)-6-nonyl-5,6-dihydro-2H-pyran-2-one
3-butyryl-4-hydroxy-6-undecyl-5,6-dihydro-2H-pyran-2-one,
4-hydroxy-3-pentanoyl-6-undecyl-5,6-dihydro-2H-pyran-2-one,
3-hexanoyl-4-hydroxy-6-nonyl-5,6-dihydro-2H-pyran-2-one,
8-(5-butyryl-4-hydroxy-6-oxo-3,6-dihydro-2H-pyran-2-yl)octanenitrile,
3-butyryl-4-hydroxy-6-(7-methoxyheptyl)-5,6-dihydro-2H-pyran-2-one,
3-butyryl-6-(2,6-dimethylhept-5-enyl)-4-hydroxy-5,6-dihydro-2H-pyran-2-one,
3-butyryl-6-(cyclopentylmethyl)-4-hydroxy-5,6-dihydro-2H-pyran-2-one,
3-(2-cyclopentylacetyl)-4-hydroxy-6-(6-methoxyhexyl)-5,6-dihydro-2H-pyran-2-one,
4-hydroxy-3-(3-methoxypropanoyl)-6-nonyl-5,6-dihydro-2H-pyran-2-one,
3-(2-cyclopropylacetyl)-4-hydroxy-6-(6-methoxyhexyl)-5,6-dihydro-2H-pyran-2-one,
4-hydroxy-6-nonyl-3-(2-(tetrahydro-2H-pyran-4-yl)acetyl)-5,6-dihydro-2H-pyran-2-one,
8-(4-hydroxy-6-oxo-5-(2-(tetrahydro-2H-pyran-4-yl)acetyl)-3,6-dihydro-2H-pyran-2-yl)octanenitrile, and
8-(5-(2-cyclohexylacetyl)-4-hydroxy-6-oxo-3,6-dihydro-2H-pyran-2-yl)octanenitrile,
or a pharmaceutically acceptable salt, stereoisomer, N-oxide or hydrate thereof.

In one embodiment, the compound is selected from the group consisting of:
3-butyryl-4-hydroxy-6-nonyl-5,6-dihydro-2H-pyran-2-one,
(R)-3-butyryl-4-hydroxy-6-nonyl-5,6-dihydro-2H-pyran-2-one,
(S)-3-butyryl-4-hydroxy-6-nonyl-5,6-dihydro-2H-pyran-2-one,
6-decyl-4-hydroxy-3-pentanoyl-5,6-dihydro-2H-pyran-2-one,
(E)-3-butyryl-6-(non-1-en-1-yl)-4-hydroxy-5,6-dihydro-2H-pyran-2-one,
4-hydroxy-6-nonyl-3-propionyl-5,6-dihydro-2H-pyran-2-one,
4-hydroxy-6-octyl-3-propionyl-5,6-dihydro-2H-pyran-2-one,
3-acetyl-4-hydroxy-6-octyl-5,6-dihydro-2H-pyran-2-one,
4-hydroxy-6-nonyl-3-pentanoyl-5,6-dihydro-2H-pyran-2-one,
3-acetyl-4-hydroxy-6-nonyl-5,6-dihydro-2H-pyran-2-one,
6-decyl-4-hydroxy-3-propionyl-5,6-dihydro-2H-pyran-2-one,
3-acetyl-6-decyl-4-hydroxy-5,6-dihydro-2H-pyran-2-one,
3-butyryl-6-decyl-4-hydroxy-5,6-dihydro-2H-pyran-2-one,
3-butyryl-4-hydroxy-6-octyl-5,6-dihydro-2H-pyran-2-one,
3-(2-cyclohexylacetyl)-4-hydroxy-6-nonyl-5,6-dihydro-2H-pyran-2-one,
4-hydroxy-3-(3-methylbutanoyl)-6-nonyl-5,6-dihydro-2H-pyran-2-one
3-butyryl-4-hydroxy-6-undecyl-5,6-dihydro-2H-pyran-2-one,
4-hydroxy-3-pentanoyl-6-undecyl-5,6-dihydro-2H-pyran-2-one,
3-hexanoyl-4-hydroxy-6-nonyl-5,6-dihydro-2H-pyran-2-one,
3-butyryl-6-(2,6-dimethylhept-5-enyl)-4-hydroxy-5,6-dihydro-2H-pyran-2-one, 3-butyryl-6-(cyclopentylmethyl)-4-hydroxy-5,6-dihydro-2H-pyran-2-one, 4-hydroxy-3-(3-methoxypropanoyl)-6-nonyl-5,6-dihydro-2H-pyran-2-one, 4-hydroxy-6-nonyl-3-(2-(tetrahydro-2H-pyran-4-yl)acetyl)-5,6-dihydro-2H-pyran-2-one, and 8-(4-hydroxy-6-oxo-5-(2-(tetrahydro-2H-pyran-4-yl)acetyl)-3,6-dihydro-2H-pyran-2-yl)octanenitrile;

or a pharmaceutically acceptable salt, stereoisomer, N-oxide or hydrate thereof.

The present inventors have found that advantageous properties may be found with compounds defined by Formula I which comprise at least one relatively long carbon chain in either the $R^1$ or the $R^2$ position. Thus, for example, if $R^1$ is $C_7$-$C_{20}$alkyl, then $R^2$ may be shorter such as $C_2$alkyl or $C_3$alkyl. Alternatively, if $R^2$ is is $C_7$-$C_{20}$alkyl, then $R^1$ may be shorter such as $C_2$alkyl or $C_3$alkyl. When the length of R1 is held constant in a series of compounds, the activity of the compounds appears to increase with the length of R2, and vice versa.

$R^3$ may be a bond to the adjacent carbon thereby defining a keto group. If $R^3$ defines such a keto group, then $R^4$ may advantageously be H, and the above-discussed relationships between the chain length of $R^1$ and $R^2$ may apply.

In other embodiments $R^3$ is H, it being appreciated that when $R^3$ is H, a depiction of the compound as a delocalized structure as illustrated below is appropriate:

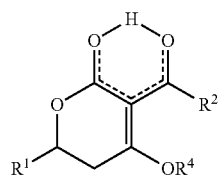

Embodiments in which $R^3$ is H in the therapeutic form represent a convenient handle to allow the compound to be derivatised with conventional prodrug moieties, such as $C(O)R^5$ (for example where $R^5$ is methyl, isopropyl, cyclopropyl or tert-butyl, any of which may be optionally fluorinated), —$CR^aR^bOR^5$, (for example where $R^a$ and $R^b$ are both H or both methyl and $R^5$ is methyl, isopropyl, cyclopropyl or tert-butyl, any of which may be fluorinated), —$CR^aR^bOC(O)R^5$, (for example where $R^a$ and $R^b$ are both H or both methyl and $R^5$ is methyl, isopropyl, cyclopropyl or tert-butyl, any of which may be optionally fluorinated), —$CR^aR^bOC(O)OR^5$, (for example where $R^a$ and $R^b$ are both H or both methyl and $R^5$ is methyl, isopropyl, cyclopropyl or tert-butyl, any of which may be optionally fluorinated) or —$C(O)CHR^7NH_2$, wherein $R^7$ is as stated above, for example $R^7$ is the side chain of an L-amino acid such as the side chain of alanine, valine, leucine or isoleucine. In alternative embodiments $R^3$ remains bound to the compound of formula I in its therapeutic form, for example when $R^3$ is $C_1$-$C_6$alkyl, (for example methyl, ethyl, isopropyl, cyclopropyl or tert-butyl, any of which may be optionally fluorinated)

$R^4$ may be H. Compounds wherein $R^4$ is H in the therapeutic form represent a convenient handle to allow the compound to be derivatised with conventional prodrug moieties, such as $C(O)R^5$ (for example where $R^5$ is methyl, isopropyl, cyclopropyl or tert-butyl, any of which may be optionally fluorinated), —$CR^aR^bOR^5$, (for example where $R^a$ and $R^b$ are both H or both methyl and $R^5$ is methyl, isopropyl, cyclopropyl or tert-butyl, any of which may be fluorinated), —$CR^aR^bOC(O)R^5$, (for example where $R^a$ and $R^b$ are both H or both methyl and $R^5$ is methyl, isopropyl, cyclopropyl or tert-butyl, any of which may be optionally fluorinated), —$CR^aR^bOC(O)OR^5$, (for example where $R^a$ and $R^b$ are both H or both methyl and $R^5$ is methyl, isopropyl, cyclopropyl or tert-butyl, any of which may be optionally fluorinated) or —$C(O)CHR^7NH_2$, wherein $R^7$ is as stated above, for example $R^7$ is the side chain of an L-amino acid such as the side chain of alanine, valine, leucine or isoleucine. In alternative embodiments $R^3$ remains bound to the compound of formula I in its therapeutic form, for example when $R^3$ is $C_1$-$C_6$alkyl, (for example methyl, ethyl, isopropyl, cyclopropyl or tert-butyl, any of which may be optionally fluorinated).

Alternatively, $R^4$ may be e.g. a methyl. If $R^4$ is a methyl, then at least one of $R^1$ and $R^2$ is longer than 3 carbons.

According to another aspect of the invention, there is provided a method of treating, eliminating and/or preventing a bacterial colonisation or infection in a subject, the method comprising the step of administering a therapeutically effective amount of a compound of Formula I, or a therapeutically acceptable salt thereof, to the subject. The method of treating, eliminating and/or preventing a bacterial infection or colonisation in a subject, may also comprise the administration of the pharmaceutical or veterinary compositions of the invention. Of especial interest is the decontamination of patients carrying MRSA by topical use of a compound of Formula I.

In the present application, the term "colonization" is understood to mean bacterial growth on any surface, such as a skin or other surface of a subject, such as a human, or the surface of implants or other medical equipment. Bacterial colonization may also be prevented using the present invention on any other objects which are at risk of obtaining such bacterial growth, such as other hospital equipment, furniture, clothing etc.

The pharmaceutical composition comprising a compound according to the invention may e.g. be used for decolonisation of skin as a preoperative measure for surgical site infection prevention.

The invention also embraces any one of the compounds of Formula I for use as a medicament.

Thus, the invention relates to e.g. a compound defined by Formula I, wherein $R^3$ is a bond, $R^4$ is H, $R^1$ is $C_6$-alkyl and $R^2$ is a methyl for use as a medicament.

According to a further aspect of the invention, there is provided the use of a compound of Formula I, or a therapeutically acceptable salt thereof, in the manufacture of medicament the treatment of a bacterial colonisation or infection in a subject.

The subject may be any subject capable of colonisation and infection by bacteria. The subject may be mammalian, or may be piscine or avian. Preferably, the subject is selected from the group comprising, but not limited to, human, canine, feline, bovine, ovine, caprine, other ruminant species, porcine, equine, avian, or piscine.

The compound of Formula I may be administered to the subject in a dose selected from the group comprising 0.1 mg/kg to 250 mg/kg body weight, typically 1 mg/kg to 100 mg/kg body weight, and more generally 5 mg/kg to 50 mg/kg body weight. Titration of dosage range to suit the infection and size and physical condition of the patient is readily achieved by the skilled general practitioner or veterinary physician. The compound of Formula I may be administered to the subject using a dosing schedule selected from the group consisting of: hourly, 3 times daily; twice daily; daily; every second day; twice weekly; once weekly;

once fortnightly; once monthly; once every two months or by constant rate or variable rate infusion. Preferably, the compound of Formula I is administered until colonisation or the signs and symptoms of infection or colonisation have at least been partially treated or alleviated.

In one embodiment, the concentration of compound of Formula I (or a metabolite) in the subject's blood after treatment is within a range selected from the group comprising, but not limited to: between 0.1 and 10 µg/mL at 2 hours, 1 and 200 µg/mL after 12 hours; between 0.1 and 5 µg/mL after 24 h; between 0.01 and 2 µg/mL after 48 hours; between 0.0001 and 1 µg/mL after 72 h. Preferably, the concentration is selected from the group comprising, but not limited to: less than 200 µg/mL after 12 hours; less than 5 µg/mL after 24 hours; less than 1 µg/L after 48 hours and less than 0.5 µg/mL after 72 hours. Selection of therapeutic dosing range and regime and titration to suit the particular infection and size and physical condition of the patient is readily achieved by the skilled general practitioner or veterinary physician.

When administered to a patient, topical formulations are envisaged, and may e.g. be convenient in relation to MRSA. Ointments, creams, wet wipes, sprays, and eye drops are alternative and illustrative ways of administering the compound according to the invention. In one embodiment, the compound according to the invention is administered by catheter to the bladder of the patient.

In one embodiment, the pharmaceutical composition comprising a compound according to the invention is prepared for nasal application, e.g. against *Staphylococcus aureus*.

The bacterial agent causing the bacterial infection may be a Gram-positive bacterial agent selected from the group comprising, but not limited to, *Staphylococcus* spp, Streptococci, *Enterococcus* spp, *Leuconostoc* spp, *Corynebacterium* spp, *Arcanobacteria* spp, *Trueperella* spp, *Rhodococcus* spp, *Bacillus* spp, Anaerobic Cocci, Anaerobic Gram-Positive Nonsporulating Bacilli, *Actinomyces* spp, *Clostridium* spp, *Nocardia* spp, *Erysipelothrix* spp, *Listeria* spp, *Kytococcus* spp, *Mycoplasma* spp, *Ureaplasma* spp, and *Mycobacterium* spp.

In one embodiment, the bacterial agent is Gram-positive and is selected from the group comprising, but not limited to, *Staphylococcus* spp. Examples of *Staphylococcus* spp include *Staphylococcus epidermidis, Staphylococcus haemolyticus, Staphylococcus lugdunensis, Staphylococcus saprophyticus, Staphylococcus auricularis, Staphylococcus capitis, Staphylococcus caprae, Staphylococcus carnosus, Staphylococcus cohnii, Staphylococcus hominis, Staphylococcus pasteuri, Staphylococcus pettenkoferi, Staphylococcus pulvereri, Staphylococcus saccharolyticus, Staphylococcus simulans, Staphylococcus schieiferi, Staphylococcus warneri, Staphylococcus xyiosus, Staphylococcus arlettae, Staphylococcus caseolyticus, Staphylococcus chromogenes, Staphylococcus condimenti, Staphylococcus delphini, Staphylococcus equorum, Staphylococcus felis, Staphylococcus fleurettii, Staphylococcus gallinarum, Staphylococcus hyicus, Staphylococcus intermedius, Staphylococcus kloosii, Staphylococcus lentus, Staphylococcus lutrae, Staphylococcus muscae, Staphylococcus nepalensis, Staphylococcus piscifermentans, Staphylococcus pseudintermedius, Staphylococcus sciuri, Staphylococcus simiae, Staphylococcus succinus*, and *Staphylococcus vitulinus*.

In another embodiment, the bacterial agent is Gram-positive and is selected from the group comprising, but not limited to, *Streptococcus* spp. Examples of *Streptococcus* spp include *Streptococcus agalactiae, Streptococcus alactolyticus, Streptococcus anginosus, Streptococcus canis, Streptococcus constellatus, Streptococcus cricetus, Streptococcus cristatus, Streptococcus downei, Streptococcus dysgalactiae* subsp. *dysgalactiae, Streptococcus dysgalactiae* subsp. *equisimilis, Streptococcus equi* subsp. *equi, Streptococcus equi* subsp. *zooepidemicus, Streptococcus ferus, Streptococcus gallolyticus* subsp. *gallolyticus* (formerly *Streptococcus bovis* biotype i), *Streptococcus gallolyticus* subsp. *pasteurianus* (formerly *Streptococcus bovis* biotype ii/2), *Streptococcus gordonii, Streptococcus hyointestinalis, Streptococcus hyovaginalis, Streptococcus infantarius, Streptococcus infantarius* subsp *infantarius, Streptococcus infantis, Streptococcus iniae, Streptococcus intermedius, Streptococcus lutetiensis* (formerly *Streptococcus bovis* biotype ii.1), *Streptococcus macaccae, Streptococcus mitis, Streptococcus mutans, Streptococcus oralis, Streptococcus orisratti, Streptococcus parasanguinis, Streptococcus peroris, Streptococcus pneumoniae, Streptococcus porcinus, Streptococcus pseudintermedius, Streptococcus pyogenes, Streptococcus ratti, Streptococcus salivarius, Streptococcus sanguinis, Streptococcus sobrinus, Streptococcus suis, Streptococcus thermophilus, Streptococcus vestibularis*, and Nutritionally Variant (Deficient) Streptococci (*Abiotrophia defectiva, Granulicatella adiacens, Granulicatella elegans*, and *Granulicatella para-adiacens*) and related species such as *Rothia mucilaginosa* (formerly *Stomatococcus mucilaginosus*) and *Pediococcus*.

In another embodiment, the bacterial agent is Gram-positive and selected from the group comprising, but not limited to, *Enterococcus* spp. Examples of *Enterococcus* spp include *Enterococcus faecalis, Enterococcus faecium, Enterococcus gallinarum, Enterococcus durans, Enterococcus avium, Enterococcus raffinosus, Enterococcus pallens, Enterococcus gilvus, Enterococcus cecorum, Enterococcus malodoratus, Enterococcus italicus, Enterococcus sanguinicola, Enterococcus mundtii, Enterococcus casseliflavus/flavescens, Enterococcus dispar, Enterococcus hirae, Enterococcus pseudoavium*, and *Enterococcus bovis*.

In another embodiment, the bacterial agent is Gram-positive and selected from the group comprising, but not limited to, *Leuconostoc* spp. Examples of *Leuconostoc* spp include *Leuconostoc mesenteroides, Leuconostoc pseudomesenteroides, Leuconostoc paramesenteroides, Leuconostoc citreum*, and *Leuconostoc lactis*.

In another preferred embodiment, the bacterial agent is *Staphylococcus aureus*, and/or strains known to be resistant such as MRSA or mupirocin resistant strain.

The bacterial agent causing the bacterial infection may be a Gram-negative bacterial agent selected from the group comprising, but not limited to, *Neisseria* spp, *Moraxella* spp, *Escherichia* spp, *Klebsiella* spp, *Proteus* spp, *Pseudomonas* spp, *Salmonella* spp, *Shigella* spp, *Campylobacter* spp, *Helicobacter* spp, *Bacteroides* spp, *Yersinia* spp, *Vibrio* spp, *Bordatella* spp and *Legionella* spp. A specific example of a Gram-negative bacterial agent causing the infection is *Acinetobacter baumannii*, as appears from the Experimental part below, see e.g. Table 2.

The bacterial agent causing the bacterial infection might be anaerobic bacteria, a spirochete or other form of bacteria including *Clostridium* spp, *Borrelia* spp, *Chlamydia* spp and *Mycoplasma* spp.

In another preferred embodiment, the bacterial agents are resistant to one or several antibiotics in present use and may be selected from, but not limited to, *Clostridium difficile*, carbapenem-resistant Enterobacteriaceae, *Neisseria gonorrhoeae*, multidrug-resistant *Acinetobacter*, drug-resistant *Campylobacter*, extended spectrum beta-lactamase producing Enterobacteriaceae, multidrug-resistant *Pseudomonas aeruginosa*, drug-resistant *Salmonella*, drug-resistant *Shigella* and drug-resistant Tuberculosis.

In another preferred embodiment, the bacterial agent is resistant to a compound selected from the group comprising: one or more of aminoglycosides (for example gentamicin); ansamycins {for example rifampicin); anti-MRSA cephalosporins (for example ceftaroline); anti-staphylococcal β-lactams (or cephamycins) (for example oxacillin or cefoxitin); carbapenems (for example ertapenem, imipenem, meropenem or doripenem); non-extended spectrum cephalosporins; 1 st and 2nd generation cephalosporins (for example cefazolin or cefuroxime); extended-spectrum cephalosporins; 3rd and 4th generation cephalosporins (for example cefotaxime or ceftriaxone); cephamycins (for example cefoxitin or cefotetan); fluoroquinolones (for example ciprofloxacin or moxifloxacin); folate pathway inhibitors (for example trimethoprim-sulphamethoxazole); fucidanes (for example fusidic acid); glycopeptides (for example vancomycin, teicoplanin or telavancin); glycylcyclines (for example tigecycline); lincosamides (for example clindamycin); lipopeptides (for example daptomycin); macrolides (for example erythromycin); monoxycarbolic acids, such as mupirocin); oxazolidinones (for example linezolid or tedizolid); phenicols (for example chloramphenicol); phosphonic acids (for example fosfomycin); streptogramins (for example quinupristin-dalfopristin); and tetracyclines (for example tetracycline, doxycycline or minocycline).

In another preferred embodiment, the bacterial agent is *Streptococcus pneumoniae*. The *Streptococcus pneumoniae* may be a strain that is resistant to one or more of β-lactams and macrolides.

In another preferred embodiment, the bacterial agent is *Streptococcus pyogenes*.

In another most preferred embodiment, the bacterial agent is *Streptococcus agalactiae*.

In another most preferred embodiment, the bacterial agent is either *Enterococcus faecium* or *Enterococcus faecalis*. The *Enterococcus faecium* or *Enterococcus faecalis* may be a strain that is resistant to aminoglycosides (for example gentamicin (high level) or streptomycin (for example streptomycin (high level)); carbapenems (for example imipenem, meropenem or doripenem); fluoroquinolones (for example ciprofloxacin, levofloxacin or moxifloxacin); glycopeptides (for example vancomycin or teicoplanin); glycylcyclines (for example tigecycline); lipopeptides (for example daptomycin); oxazolidinones (for example linezolid); penicillins (for example ampiciilin); streptogramins (for example quinupristin-dalfopristin); tetracycline (for example doxycycline or minocycline).

In another embodiment, the bacterial agent is *Clostridium difficile*.

The bacterial infection in the subject may cause a disease selected from the group comprising, but not limited to, nosocomial pneumonia caused by *Staphylococcus aureus* (MDR, XDR, PDR or methicillin-susceptible or -resistant strains), or invasive pneumococcal diseases such as pneumonia, bronchitis, acute sinusitis, otitis media, conjunctivitis, meningitis, bacteremia, sepsis, osteomyelitis, septic arthritis, endocarditis, peritonitis, pericarditis, cellulitis, and brain abscess caused by *Streptococcus pneumoniae* (including multi-drug resistant strains [MDRSP] such as those resistant to β-lactams and macrolides), complicated skin and skin structure infections, including diabetic foot infections, with or without concomitant osteomyelitis, caused by *Staphylococcus aureus* (methicillin-susceptible and -resistant strains), *Streptococcus pyogenes*, or *Streptococcus agalactiae*, uncomplicated skin and skin structure infections caused by *Staphylococcus aureus* (methicillin-susceptible and -resistant strains) or *Streptococcus pyogenes*, community-acquired pneumonia caused by *Streptococcus pneumoniae* (including multi-drug resistant strains [MDRSP], including cases with concurrent bacteraemia, or *Staphylococcus aureus* (methicillin-susceptible and -resistant strains) and *Staphylococcus aureus* bloodstream Infections (bacteraemia), including those with right-sided infective endocarditis, caused by methicillin-susceptible and methicillin-resistant isolates, vancomycin-resistant *enterococcus* infections, including cases with concurrent bacteraemia, and treatment of *Clostridium* d/f/c//e-associated diarrhea (CDAD).

In another preferred embodiment, a compound of the invention, or a therapeutically acceptable salt thereof, is administered together with a compound or agent that removes or substantially removes or reduces the integrity of the cell wall of the bacterial agent. As an example, the compound is selected from the group consisting of: P lactams, fosfomycin, lysozyme, polymyxins and chelating agents such as ethylenediaminetetraacetic acid (EDTA). As an example, the agent is an immunological agent (such as an antibody or vaccine) that reduces the integrity of the cell wall. In one preferred embodiment, the compound, or a therapeutically acceptable salt thereof, is administered together with a compound that removes or substantially removes or weakens the integrity of the outer cell wall of a Gram-negative bacterial agent.

According to another aspect of the invention, there is provided an antibacterial pharmaceutical composition comprising a therapeutically effective amount of a compound of Formula I, or a therapeutically acceptable salt thereof. Preferably, the composition is an antibacterial pharmaceutical composition.

According to another aspect of the invention, there is provided an antibacterial veterinary composition comprising a therapeutically effective amount of a compound of Formula I, or a therapeutically acceptable salt thereof. Preferably, the composition is an anti-bacterial veterinary composition, for topical or oral use.

The pharmaceutical composition may optionally include a pharmaceutically acceptable excipient or carrier. The veterinary composition may optionally include a veterinary acceptable excipient or carrier.

In another embodiment, the pharmaceutical or veterinary composition comprises impurities, wherein the quantity of impurities as a percentage of the total weight of the composition is selected from the group consisting of: less than 20% impurities (by total weight of the composition); less than 15% impurities; less than 10% impurities; less than 8% impurities; less than 5% impurities; less than 4% impurities; less than 3% impurities; less than 2% impurities; less than 1% impurities; less than 0.5% impurities; less than 0.1% impurities. In one embodiment, the pharmaceutical or veterinary composition comprises microbial impurities or secondary metabolites, wherein the quantity of microbial impurities as a percentage of the total weight of the composition is selected from the group consisting of: less than 5%; less than 4%; less than 3%; less than 2%; less than 1%; less than 0.5%; less than 0.1%; less than 0.01%; less than 0.001%. In one embodiment, the pharmaceutical or veterinary composition is sterile and stored in a sealed and sterile container. In one embodiment, the pharmaceutical or veterinary composition contains no detectable level of microbial contamination.

The pharmaceutical or veterinary composition of the invention may comprise a further antimicrobial agent. The further antimicrobial agent may be an antifungal agent or antibacterial agent. The method of treating or preventing a bacterial infection or colonisation in a subject, may also comprise the administration of a compound of the invention with a further antimicrobial agent.

In one embodiment, the pharmaceutical composition comprises a compound according to the invention in combination with mupirocin. Such a composition may e.g. be for topical application, for example an ointment, or any other form as discussed elsewhere in this application.

The pharmaceutical or veterinary composition of the invention may comprise more than one compound of the invention, such as a combination of compounds. The method of treating or preventing a bacterial infection or colonisation in a subject may also comprise the administration of more than one compound of the invention.

In one embodiment, the antifungal agent is selected from the group comprising, but not limited to naturally occurring agents including Echinocandins (Anidulafungin, Caspofungin, Micafungin), Polyenes (Amphotericin B, Candicidin, Filipin, Fungichromin (Pentamycin), Hachimycin, Hamycin, Lucensomycin, Mepartricin, Natamycin, Nystatin, Pecilocin, Perimycin), and other naturally occurring antifungal agents including Griseofulvin, Oligomycins, Pyrrolnitrin, Siccanin, and Viridin. The antifungal agent may be a synthetic compound selected from the group comprising, but not limited to Allylamines (Butenafine, Naftifine, Terbinafine) Imidazoles (Bifonazole, Butoconazole, Chlormidazole, Climbazole, Croconazole (Cloconazole), Clotrimazole, Eberconazole, Econazole, Enilconazole, Fenticonazole, Flutrimazole, Fosfluconazole, Isoconazole, Ketoconazole, Lanoconazole, Luliconazole, Miconazole, Neticonazole, Omoconazole, Oxiconazole Nitrate, Parconazole, Sertaconazole, Sulconazole, Tioconazole), Thiocarbamates (Liranaftate, Tolciclate, Tolindate, Tolnaftate), Triazoles (Fluconazole, Isavuconazole, Itraconazole, Posaconazole, Ravuconazole, Saperconazole, Terconazole, Voriconazole), and other synthetic agents such as Acrisorcin, Amorolfine, Bromosalicylchloranilide (Bromochlorosalicylanilide), Buclosamide, Calcium Propionate, Chlorphenesin, Ciclopirox, Cloxyquin (Cloxiquine), Coparaffinate, Exalamide, Flucytosine, Haloprogin, Hexetidine, Loflucarban, Nifuratel, Nifuroxime, Piroctone, Potassium Iodide, Propionic Acid, Pyrithione, Salicylanilide, Sodium Parachlorobenzoate, Sodium Propionate, Sulbentine, Tenonitrozole, Triacetin, Trimetrexate, Undecylenic Acid (Undecenoic Acid), and Zinc Propionate.

The composition of the invention may comprise an antibiotic adjunct selected from the group comprising, but not limited to, β-Lactamase Inhibitors (Avibactam, Clavulanic Acid, Sulbactam, Sultamicillin, Tazobactam), Renal Dipeptidase Inhibitors (Cilastatin), and Renal Protectant (Betamipron).

In one embodiment, the composition of the invention comprises a further antibiotic selected from the group comprising, but not limited to,
2,4-DIAMINOPYRIMIDINES, including Baquiloprim, Brodimoprim, Iclaprim, Ormetoprim, Pyrimethamine, Tetroxoprim, Trimethoprim;
AMINOCOUMARINS, including Novobiocin;
AMINOCYCLITOLS, including Spectinomycin;
AMINOGLYCOSIDES, including Amikacin, Apramycin, Arbekacin, Bekanamycin, Butirosin, Dibekacin, Dihydrostreptomycin, Etimicin, Fortimicins (Astromicin), Framycetin, Gentamicin, Hygromycin B, Isepamicin, Kanamycin, Micronomicin, Neomycin, Netilmicin, Paromomycin, Plazomicin, Ribostamycin, Sisomicin, Streptomycin, Tobramycin, Verdamicin;
AMINOMETHYLCYCLINES, including Omadacycline;
AMPHENICOLS, including Azidamfenicol, Chloramphenicol, Florfenicol, Thiamphenicol;
ANSAMYCINS, including Rifabutin, Rifamide, Rifampin (Rifampicin), Rifamycin, Rifapentine, Rifaximin;
ANTISEPTIC AGENTS, including Acridine derivatives (including acriflavine, aminoacridine, ethacridine, proflavine), Bispyridines (including octenidine dihydrochloride), Brominated salicylanilides (including bromsalans), Chlorhexidine, Phenol derivatives (including thymol and triclosan), Quarternary ammonium compounds (including Alkyldimethylethylbenzyi Ammonium Chloride, benzalkonium chloride, cetylpyridinium chloride, benzethonium chloride, cetrimonium);
ANTITUBERCULAR AGENTS, including Cycloserine, Delamanid, Ethambutol, Ethionamide, Isoniazid (Ftivazide), Morinamide, p-Aminosalicylic Acid (PAS), Protionamide, Pyrazinamide, Terizidone, Thioacetazone, Tiocarlide;
ARSENICALS, including Arsanilic Acid, Roxarsone;
BACTERIOCINS, including Nisin, Brilacidin (PMX-30063);
β-LACTAM CARBACEPHEMS, including Loracarbef;
β-LACTAM CARBAPENEMS, including Biapenem, Doripenem, Ertapenem, Faropenem, Imipenem, Meropenem, Panipenem, Razupenem, Ritipenem, Sulopenem, Tebipenem, Tomopenem;
β-LACTAM CEPHALOSPORINS, including Cefacetrile, Cefaclor, Cefadroxil, Cefalexin, Cefaloglycin, Cefalonium, Cefaloridine, Cefalothin, Cefamandole, Cefapirin, Cefatrizine, Cefazaflur, Cefazedone, Cefazolin, Cefcapene, Cefdinir, Cefditoren, Cefepime, Cefetamet, Cefixime, Cefmenoxime, Cefodizime, Cefonicid, Cefoperazone, Ceforanide, Cefoselis, Cefotaxime, Cefotiam, Cefovecin, Cefozopran, Cefpimizole, Cefpiramide, Cefpirome, Cefpodoxime, Cefprozil, Cefquinome, Cefradine, Cefroxadine, Cefsulodin, Ceftaroline, Ceftazidime, Cefteram, Ceftezole, Ceftibuten, Ceftiofur, Ceftizoxime, Ceftobiprole, Ceftolozane, Ceftradine, Ceftrezole, Ceftriaxone, Ceftroxadine, Cefuroxime, Cefuzonam, Pivcefalexin;
β-LACTAM CEPHAMYCINS, including Cefbuperazone, Cefmetazole, Cefminox, Cefotetan, Cefoxitin; β-LACTAM MONOBACTAMS, including Aztreonam, Carumonam, Tigemonam;
β-LACTAM OXACEPHEMS, including Flomoxef, Latamoxef, Moxalactam;
β-LACTAM PENICILLINS, including Amdinocillin (Mecillinam), Amoxicillin, Ampicillin, Apalcillin, Aspoxicillin, Azidocillin, Azlociliin, Bacampicillin, Carbenicillin, Carindacillin, Ciclacillin, Clemizole Penicillin, Clometocillin, Cloxacillin, Cyclacillin, Dicloxacillin, Epicillin, Fenbenicillin, Floxacillin (Flucloxacillin), Hetacillin, Lenampicillin, Mecillinam, Metampicillin, Methicillin Sodium, Mezlocillin, Nafcillin, Oxacillin, Penamecillin, Penethamate Hydriodide, Penicillin G, Penicillin G Benzathine, Penicillin G Procaine, Penicillin N, Penicillin O, Penicillin V, Phenethicillin Potassium, Piperacillin, Pivampicillin, Pivmecillinam, Propicillin, Quinacillin, Sulbenicillin, Sultamicillin, Talampicillin, Temocillin, Ticarcillin;
BICYCLOMYCINS, including Bicozamycin;
BORON CONTAINING ANTIBACTERIAL AGENTS, including AN3365 (aminomethylbenzoxaboroles), GSK2251052 (leucyl-tRNA synthetase inhibitors);
CYCLIC ESTERS, including Fosfomycin;
EFFLUX PUMP INHIBITORS;

FATTY ACID SYNTHESIS INHIBITORS (FabI), AFN-1252, MUT056399, FAB-001 FLUOROQUINOLONES, including Avarofloxacin, Balofloxacin, Besifloxacin, Chinfloxacin, Cinoxacin, Ciprofloxacin, Clinafloxacin, Danofloxacin, Delafloxacin, Difloxacin, Enoxacin, Enrofloxacin, Finafloxacin, Fleroxacin, Flumequine, Garenoxacin, Gatifloxacin, Gemifloxacin, Grepafloxacin, Ibafloxacin, Levofloxacin, Lomefloxacin, Marbofloxacin, Miloxacin, Moxifloxacin, Nadifloxacin, Norfloxacin, Ofloxacin, Orbifloxacin, Pazufloxacin, Pefloxacin, Pradofloxacin, Prulifloxacin, Rosoxacin, Rufloxacin, Sarafloxacin, Sitafloxacin, Sparfloxacin, Temafloxacin, Tosufloxacin, Trovafloxacin, Zabofloxacin;

FUSIDANES, including Fusidic Acid;

GLYCOLIPODEPSIPEPTIDE, including Ramoplanin;

GLYCOPEPTIDES, including Avoparcin, Dalbavancin, Norvancomycin, Oritavancin, Teicoplanin, Telavancin, Vancomycin;

GLYCOPHOSPHOLIPIDS, including Bambermycins (bambermycin, moenomycins, flavophospholipol);

GLYCYLCYCLINES, including Tigecycline;

HYBRIDS, Cadazolid (Oxazolidinone-quinolone), TD-1792 (glycopeptide-cephalosporin);

LINCOSAMIDES, including Clindamycin, Lincomycin, Pirlimycin;

LIPOPEPTIDES, including Daptomycin, Surotomycin;

MACROLIDES, including Azithromycin, Carbomycin, Cethromycin, Clarithromycin, Dirithromycin, Erythromycin, Fidaxomicin, Flurithromycin, Gamithromycin, Josamycin, Kitasamycin, Leucomycin, Meleumycin, Midecamycins, Miokamycin, Mirosamycin, Oleandomycin, Primycin, Rokitamycin, Rosaramicin, Roxithromycin, Sedecamycin, Solithromycin, Spiramycin, Telithromycin, Terdecamycin, Tildipirosin, Tilmicosin, Troleandomycin, Tulathromycin, Tylosin, Tylvalosin;

NITROFURANS, including Furaltadone, Furazidin, Furazolidone, Furazolium Chloride, Nifuratel, Nifurfoline, Nifuroxazide, Nifurpirinol, Nifurtoinol, Nifurzide, Nitrofural, Nitrofurantoin, Nitrofurazone;

NITROIMIDAZOLES, including Dimetridazole, Metronidazole, Ornidazole, Ronidazole, Secnidazole, Tinidazole;

OLIGOSACCHARIDES, including Avilamycin, Everninomicin;

OTHER ANTIBACTERIAL AGENTS, including Auriclosene, Chloroxine, Chlorquinaldol, Clioquinol, Clofoctol, Halquinol, Lotilibcin, Mandelic Acid, Methenamine (hexamine), Nitazole, Nitroxoline, Perchlozone, Taurolidine, Thenoic Acid, Xibornol;

OXAZOLID1NONES, including Eperezolid, Linezolid, Posizolid, Radezolid, Sutezolid, Tedizolid (Torezolid);

PEPTIDE DEFORMYLASE INHIBITORS, including GSK1322322;

PEPTIDES, including Omiganan, Pexiganan;

PLEUROMUTILINS, including Retapamulin, Tiamulin, Valnemulin;

POLYETHER IONOPHORES, including Laidlomycin, Lasalocid, Maduramicin, Monensin, Narasin, Salinomycin, Semduramicin;

POLYMYXINS, including Colistin, Polymyxin B;

POLYPEPTIDES, including Amphomycin, Bacitracin, Capreomycin, Enduracidin, Enramycin, Enviomycin, Fusafungine, Gramicidin(s), Iseganan, Magainins, Nosiheptide, Ristocetin, Thiostrepton, Tuberactinomycin, Tyrocidine, Tyrothricin, Viomycin;

PSEUDOMONIC ACIDS, including Mupirocin;

QUINOLONES, including Nalidixic Acid, Nemonoxacin, Oxolinic Acid, Ozenoxacin, Pipemidic Acid, Piromidic Acid;

QUINOXALINES, including Carbadox, Olaquindox;

RIMINOFENAZINES, including Clofazimine;

STATINS, including Atorvastatin, Fluvastatin, Lovastatin, Mevastatin, Pitavastatin, Pravastatin, Rosuvastatin, Simvastatin;

STREPTOGRAMINS, including Dalfopristin, Flopristin, Linopnstin, Pristinamycin, Quinupristin, Virginiamycin;

STREPTOTHRICINS, including Nourseothricin;

SULFONAMIDES, including Acetyl Sulfamethoxypyrazine, Chloramine-B, Chloramine-T, Dichloramine T, Formosulfathiazole, Mafenide, N4-Sulfanilylsulfanilamide, Noprylsulfamide, N-Sulfanilyl-3,4-xylamide, Ormaosulfathiazole, Phthalylsulfacetamide, Phthalylsulfathiazole, Salazosulfadimidine, Succinylsulfathiazole, Sulfabenzamide, Sulfacarbamide, Sulfacetamide, Sulfachlorpyridazine, Sulfachrysoidine, Sulfaclozine, Sulfacytine, Sulfadiazine, Sulfadicramide, Sulfadimethoxine, Sulfadimidine, Sulfadoxine, Sulfaethidole, Sulfaguanidine, Sulfaguanole, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfamethylthiazole, Sulfametopyrazine, Sulfametrole, Sulfamidochrysoidine, Sulfamonomethoxine, Sulfamoxole, Sulfanilamide, Sulfanilylurea, Sulfaperine, Sulfaphenazole, Sulfaproxyline, Sulfapyrazine, Sulfapyridine, Sulfaquinoxaline, Sulfathiazole, Sulfathiourea, Sulfatroxazole, Sulfisomidine, Sulfisoxazole (Sulfafurazole);

SULFONES, including Acediasulfone, Dapsone, Glucosulfone Sodium, p-Sulfanilylbenzylamine, Succisulfone, Sulfanilic Acid, Sulfoxone Sodium, Thiazolsulfone;

TETRACYCLINES, including Chlortetracycline, Clomocycline, Demeclocycline, Doxycycline, Eravacycline, Guamecycline, Lymecycline, Meclocycline, Methacycline, Minocycline, Oxytetracycline, Penimepicycline, Pipacycline, Rolitetracycline, Sarecycline, and Tetracycline.

The composition of the invention may further comprise an excipient selected from the group comprising, but not limited to, binders and compression aids, coatings and films, colouring agents diluents and vehicles disintegrants, emulsifying and solubilising agents, flavours and sweeteners, repellents, glidants and lubricants, plasticisers, preservatives, propellants, solvents, stabilisers, suspending agents and viscosity enhancers.

According to a further aspect of the invention, there is provided a medical device when used in a method of treating or preventing a bacterial infection in the subject.

According to further aspect of the invention, there is provided a medical device comprising the composition of the invention. The composition of the invention may be any slow release form, and/or in the form of a coating of the medical device.

The medical device may be in a form selected from the group comprising: an implant, a plaster, a bandage, and other dressing applied to a bacterial infection in a subject.

According to further aspect of the invention, there is provided a method of killing bacteria, the method including the step of contacting the bacteria with a compound of the invention, or a therapeutically acceptable salt thereof. As discussed elsewhere in the present application, administration may e.g. be by creme, ointment, eye drops or by catheter to the bladder of the patient.

According to further aspect of the invention, there is provided the use of a compound of the invention, or a therapeutically acceptable salt thereof, to kill bacteria, said use comprising the step of contacting the bacteria with a compound of the invention, or a therapeutically acceptable salt thereof.

DESCRIPTION OF EMBODIMENTS

General

Before describing the present invention in detail, it is to be understood that the invention is not limited to particular exemplified methods or compositions disclosed herein. It is also to be understood that the terminology used herein is for the purpose of describing particular embodiments of the invention only, and is not intended to be limiting.

All publications referred to herein, including patents or patent applications, are incorporated by reference in their entirety. However, applications that are mentioned herein are referred to simply for the purpose of describing and disclosing the procedures, protocols, and reagents referred to in the publication which may have been used in connection with the invention. The citation of any publications referred to herein is not to be construed as an admission that the invention is not entitled to antedate such disclosure by virtue of prior invention.

In addition, the carrying out of the present invention makes use of, unless otherwise indicated, conventional microbiological techniques within the skill of the art. Such conventional techniques are known to the skilled worker.

As used herein, and in the appended claims, the singular forms "a", "an", and "the" include the plural unless the context clearly indicates otherwise.

Unless otherwise indicated, all technical and scientific terms used herein have the same meanings as commonly understood by one of ordinary skill in the art to which this invention belongs. Although any materials and methods similar to, or equivalent to, those described herein may be used to carry out the present invention, the preferred materials and methods are herein described.

The invention described herein may include one or more ranges of values (e.g. size, concentration, dose etc). A range of values will be understood to include all values within the range, including the values defining the range, and values adjacent to the range that lead to the same or substantially the same outcome as the values immediately adjacent to that value which define the boundary of the range.

The pharmaceutical or veterinary compositions of the invention may be administered in a variety of unit dosages depending on the method of administration, target site, physiological state of the patient, and other medicaments administered. For example, unit dosage form suitable for oral administration include solid dosage forms such as powder, tablets, pills, and capsules, and liquid dosage forms, such as elixirs, syrups, solutions and suspensions. The active ingredients may also be administered parenterally in sterile liquid dosage forms. Gelatin capsules may contain the active ingredient and inactive ingredients such as powder carriers, glucose, lactose, sucrose, mannitol, starch, cellulose or cellulose derivatives, magnesium stearate, stearic acid, sodium saccharin, talcum, magnesium carbonate, and the like. Topical forms were discussed above and are included as an alternative in all aspects of the present invention.

The phrase "therapeutically effective amount" as used herein refers to an amount sufficient to inhibit bacterial growth associated with a bacterial infection or colonisation. That is, reference to the administration of the therapeutically effective amount of a compound of Formula I according to the methods or compositions of the invention refers to a therapeutic effect in which substantial bacteriocidal or bacteriostatic activity causes a substantial inhibition of bacterial infection. The term "therapeutically effective amount" as used herein, refers to a sufficient amount of the composition to provide the desired biological, therapeutic, and/or prophylactic result. The desired results include elimination of bacterial infection or colonisation or reduction and/or alleviation of the signs, symptoms, or causes of a disease, or any other desired alteration of a biological system. An effective amount in any individual case may be determined by one of ordinary skill in the art using routine experimentation. In relation to a pharmaceutical or veterinary composition, effective amounts can be dosages that are recommended in the modulation of a diseased state or signs or symptoms thereof. Effective amounts differ depending on the composition used and the route of administration employed. Effective amounts are routinely optimized taking into consideration pharmacokinetic and pharmacodynamic characteristics as well as various factors of a particular patient, such as age, weight, gender, etc and the area affected by disease or disease causing microbes.

As referred to herein, the terms "treatment" or "treating" refers to the full or partial removal of the symptoms and signs of the condition as well as any trace or sign of the causing bacteria. For example, in the treatment of a bacterial infection or colonisation, the treatment completely or partially removes the signs of the infection as well as any bacteria as such. Preferably in the treatment of infection, the treatment reduces or eliminates the infecting bacterial pathogen leading to microbial cure, and prevention of transmission of any serious development of the infection. The term "elimination" refers herein to the total removal of all signs and trace of an infection.

As referred to herein, the term "bacteria" refers to members of a large domain of prokaryotic microorganisms. Typically a few micrometers in length, bacteria have a number of shapes, ranging from spheres to rods and spirals and can be present as individual cells or present in linear chains or clusters of variable numbers and shape. Preferably the terms "bacteria" and its adjective "bacterial" refer to bacteria such as the Gram-positive *Staphylococcus* spp, *Streptocccus* spp, *Bacillus* spp, *Enferococcus* spp, *Listeria* spp, and anaerobic bacteria; The terms may refer to an antibiotic-sensitive strain or an antibiotic-resistant strain. In a preferred embodiment, the terms refer to MRSA or MRSP. In another preferred embodiment, the terms refer to MDR *Staphylococcus* spp, *Streptococcus* spp, *Enterococcus* spp, *Clostridium difficile*. The term may also refer to Gram-negative bacteria such as *Enterobaceriaceae* spp, *Klebsiella* spp, *Neisseria* spp, *Acinetobacter* spp, *Campylobacter* spp, *Salmonella* spp, *Shigella* spp, *Pseudomonas* spp.

Referred to herein, the term "methicillin-resistant bacteria" (such as methicillin-resistant *Staphylococcus*) refers a bacteria isolate that demonstrates resistance at any dose to all 3-lactams including penicillins, carbapenems and first to fourth generation cephalosporins, but not to the fifth generation anti-MRSA cephalosporins (for example ceftaroline). Multidrug-resistant (MDR) is defined as acquired non-susceptibility to at least one agent in three or more antimicrobial categories, extensively drug-resistant (XDR) is defined as non-susceptibility to at least one agent in all but two or fewer antimicrobial categories (i.e. bacterial isolates remain susceptible to only one or two categories) and pandrug-resistant (PDR) is defined as non-susceptibility to all agents in all antimicrobial categories currently available.

An example of susceptible, MDR, XDR and PDR bacteria includes the following. Wild type, antibacterial unexposed isolates of *Staphylococcus aureus* that are likely to be susceptible to all of the following antibacterial categories (and agents); aminoglycosides (for example gentamicin); ansamycins (for example rifampicin); anti-MRSA cephalosporins (for example ceftaroline); anti-staphylococcal β-lactams (or cephamycins) (for example oxacillin or cefoxitin); carbapenems (for example ertapenem, imipenem, meropenem or doripenem); non-extended spectrum cephalosporins; 1 st and 2nd generation cephalosporins (for example cefazolin or cefuroxime); extended-spectrum cephalosporins; 3rd and 4th generation cephalosporins (for example cefotaxime or ceftriaxone); cephamycins (for example cefoxitin or cefotetan); fluoroquinolones (for example ciprofloxacin or moxifloxacin); folate pathway inhibitors (for example trimethoprim-sulphamethoxazole); fucidanes (for example fusidic acid); glycopeptides (for example vancomycin, teicoplanin or telavancin); glycylcyclines (for example tigecycline); lincosamides (for example clindamycin); lipopeptides (for example daptomycin); macrolides (for example erythromycin); oxazolidinones (for example linezolid or tedizolid); phenicols (for example chloramphenicol); phosphonic acids (for example fosfomycin); streptogramins (for example quinupristin-dalfopristin; and tetracyclines (for example tetracycline, doxycycline or minocycline). Isolates that are non-susceptible to more than one agent in more than three antimicrobial categories are classified as MDR (all MRSA, for example, meet the definition of MDR). Isolates that are non-susceptible to more than one agent in all but one or two antimicrobial categories are classified as XDR. Isolates that are non-susceptible to all listed antibacterial agents are PDR.

The use of compounds according to the invention, as defined by Formula I, avoids the use of other antibiotics and thus resistance development to such antibiotics.

Pharmaceutically and veterinary acceptable salts include salts which retain the biological effectiveness and properties of the compounds of the present disclosure and which are not biologically or otherwise undesirable. In many cases, the compounds disclosed herein are capable of forming acid and/or base salts by virtue of the presence of amino and/or carboxyl groups or groups similar thereto. Acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as by way of example only, alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri (substituted alkenyl) amines, cycloalkyl amines, di(cycloalkyl) amines, tri(cycloalkyl) amines, substituted cycloalkyl amines, disubstituted cycloalkyl amines, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diary' amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Pharmaceutically and veterinary acceptable acid addition salts may be prepared from inorganic and organic acids. The inorganic acids that can be used include, by way of example only, hydrochloric acid, hydrobromic acid, sulfuric acid, nitric acid, phosphoric acid, and the like. The organic acids that can be used include, by way of example only, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The pharmaceutically or veterinary acceptable salts of the compounds useful in the present disclosure can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences. 17th ed., Mack Publishing Company, Easton, Pa. (1985), p. 1418, the disclosure of which is hereby incorporated by reference. Examples of such acceptable salts are the iodide, acetate, phenyl acetate, trifluoroacetate, acrylate, ascorbate, benzoate, chlorobenzoate, dinitrobenzoate, hydroxybenzoate, methoxybenzoate, methyl benzoate, o-acetoxybenzoate, naphthalene-2-benzoate, bromide, isobutyrate, phenylbutyrate, γ-hydroxybutyrate, β-hydroxybutyrate, butyne-I,4-dioate, hexyne-I,4-dioate, hexyne-I,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesu!fonate, ethanesulfonate, 2-hydroxyethanesulfonate, merhanesulfonate, naphthalene-I-sulfonate, naphthalene-2-sulfonate, p-toluenesulfonate, xylenesulfonate, tartarate, and the like.

The present invention also includes isotope-labelled compounds of formula I or any subgroup of formula I, wherein one or more of the atoms is replaced by an isotope of that atom, i.e. an atom having the same atomic number as, but an atomic mass different from, the one(s) typically found in nature. Examples of isotopes that may be incorporated into the compounds of formula I or any subgroup of formula I, include but are not limited to isotopes of hydrogen, such as $^2$H and $^3$H (also denoted D for deuterium and T for tritium, respectively), carbon, such as $^{11}$C, $^{13}$C and $^{14}$C, nitrogen, such as $^{13}$N and $^{15}$N, oxygen, such as $^{15}$O, $^{17}$O and $^{18}$O, phosphorus, such as $^{31}$P and $^{32}$P, sulfur, such as $^{35}$S, fluorine, such as $^{18}$F, chlorine, such as $^{36}$Cl, bromine such as $^{75}$Br, $^{76}$Br, $^{77}$Br and $^{82}$Br, and iodine, such as $^{123}$I, $^{124}$I, $^{125}$I and $^{131}$I. The choice of isotope included in an isotope-labelled compound will depend on the specific application of that compound. For example, for drug or substrate tissue distribution assays, compounds wherein a radioactive isotope such as $^3$H or $^{14}$C is incorporated will generally be most useful. For radio-imaging applications, for example positron emission tomography (PET) a positron emitting isotope such as $^{11}$C, $^{18}$F, $^{13}$N or $^{15}$O will be useful. The incorporation of a heavier isotope, such as deuterium, i.e. $^{2}$H, may provide greater metabolic stability to a compound of formula I or any subgroup of formula I, which may result in, for example, an increased in vivo half-life of the compound or reduced dosage requirements.

Isotope-labelled compounds of formula I or any subgroup of formula I can be prepared by processes analogous to those described in the Schemes and/or Examples herein below by using the appropriate isotope-labelled reagent or starting material instead of the corresponding non-isotope-labelled reagent or starting material, or by conventional techniques known to those skilled in the art.

The compounds of the invention can have one or several chiral centers and may exist and be isolated in optically active and racemic forms. Some compounds may exhibit polymorphism. It is to be understood that any racemic, optically active, diastereomeric, polymorphic or stereoisomeric form or mixtures thereof, of a compound provided herein is within the scope of this invention. The absolute configuration of such compounds can be determined using methods known in the art such as, for example, X-ray diffraction or NMR and/or implication from starting materials of known stereochemistry and/or stereoselective synthesis methods. Pharmaceutical compositions in accordance with the invention will preferably comprise substantially stereoisomerically pure preparations of the indicated stereoisomer.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by using procedures well known in the art. For instance, enantiomers may be separated from each other by resolution of the racemic mixture, i.e. formation of a diastereomeric salt effected by reaction with an optically active acid or base followed by selective crystallization of the formed diastereomeric salt. Examples of such acids are tartaric acid, dibenzoyltartaric acid, ditoluoyltartaric acid and camphorsulfonic acid. Alternatively, enantiomers may be separated by chromatographic techniques using chiral stationary phases. Pure stereochemically isomeric forms may also be obtained by synthesis from stereochemically pure forms of the appropriate starting materials, provided that the reaction occurs stereospecifically, by chiral synthesis or by utilisation of a chiral auxiliary. If a specific stereoisomer is desired, the preparation of that compound is preferably performed using stereospecific methods. These methods will advantageously employ enantiomerically pure starting materials.

Diastereomeric racemates of the compounds of the invention can be separated by conventional methods. Appropriate physical separation methods that may advantageously be employed are, for example, selective crystallization and chromatography, e.g. column chromatography.

The terms and expressions used herein throughout the abstract, specification and claims shall be interpreted as defined below unless otherwise indicated. The meaning of each term is independent at each occurrence. These definitions apply regardless of whether a term is used by itself or in combination with other terms, unless otherwise indicated. A term or expression used herein which is not explicitly defined, shall be interpreted as having its ordinary meaning used in the art. Chemical names, common names, and chemical structures may be used interchangeably to describe the same structure. If a chemical compound is referred to using both a chemical structure and a chemical name and an ambiguity exists between the structure and the name, the structure predominates.

"$C_m$-$C_n$alkyl" on its own or in composite expressions such as $C_m$-$C_n$haloalkyl, $C_m$-$C_n$alkylcarbonyl, $C_m$-$C_n$alkylamine, etc. represents a straight or branched aliphatic hydrocarbon radical having the number of carbon atoms designated, e.g. $C_1$-$C_4$alkyl means an alkyl radical having from 1 to 4 carbon atoms. $C_1$-$C_6$alkyl has a corresponding meaning, including also all straight and branched chain isomers of pentyl and hexyl. Preferred alkyl radicals for use in the present invention are $C_1$-$C_6$alkyl, including methyl, ethyl, n-propyl, isopropyl, n-butyl, isobutyl, sec-buty, tert-butyl, n-pentyl and n-hexyl, especially $C_1$-$C_4$alkyl such as methyl, ethyl, n-propyl, isopropyl, tert-butyl, n-butyl and isobutyl. Methyl and isopropyl are typically preferred. An alkyl group may be unsubstituted or substituted by one or more substituents which may be the same or different, each substituent being independently selected from the group consisting of halo, alkenyl, alkynyl, aryl, cycloalkyl, cyano, hydroxy, $C_m$-$C_n$alkoxy, —O-aryl, —$C_m$-$C_n$alkoxy$C_m$-$C_n$alkyl, $C_m$-$C_n$alkylthio, —NH$_2$, —NH($C_m$-$C_n$alkyl), —N($C_m$-$C_n$alkyl)$_2$, —NH(cycloalkyl), —OC(O)alkyl, —O—C(O) aryl, —O—C(O)cycloalkyl, —C(O)OH and —C(O)OC$_m$-$C_n$alkyl. It is generally preferred that the alkyl group is unsubstituted, unless otherwise indicated.

"$C_2$-$C_n$alkenyl" represents a straight or branched aliphatic hydrocarbon radical containing at least one carbon-carbon double bond and having the number of carbon atoms designated, e.g. $C_2$-$C_4$alkenyl means an alkenyl radical having from 2 to 4 carbon atoms; $C_2$-$C_6$alkenyl means an alkenyl radical having from 2 to 6 carbon atoms. Non-limiting alkenyl groups include ethenyl, propenyl, n-butenyl, 3-methylbut-2-enyl, n-pentenyl and hexenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, alkoxy, —O-aryl, alkoxyalkyl, alkylthio, —NH$_2$, —NH($C_m$-$C_n$alkyl), —N($C_m$-$C_n$alkyl)$_2$, —NH($C_3$-$C_n$cycloalkyl), —OC(O)$C_m$-$C_n$alkyl, —O—C(O)aryl, —O—C (O)$C_3$-$C_n$cycloalkyl, —C(O)OH and —C(O)OC$_m$-$C_n$alkyl. It is generally preferred that the alkenyl group is unsubstituted, unless otherwise indicated.

"$C_2$-$C_n$alkynyl" represents a straight or branched aliphatic hydrocarbon radical containing at least one carbon-carbon triple bond and having the number of carbon atoms designated, e.g. $C_2$-$C_4$alkynyl means an alkynyl radical having from 2 to 4 carbon atoms; $C_2$-$C_6$alkynyl means an alkynyl radical having from 2 to 6 carbon atoms. Non-limiting alkenyl groups include ethynyl, propynyl, 2-butynyl and 3-methylbutynyl pentynyl and hexynyl. An alkynyl group may be unsubstituted or substituted by one or more substituents which may be the same or different, each substituent being independently selected from the group consisting of halo, $C_2$-$C_n$alkenyl, $C_2$-$C_n$alkynyl, aryl, $C_3$-$C_n$cycloalkyl, cyano, hydroxy, $C_m$-$C_n$alkoxy, —O-aryl, —$C_m$-$C_n$alkoxy$C_m$-$C_n$alkyl, $C_m$-$C_n$alkylthio, —$NH_2$, —NH($C_m$-$C_n$alkyl), —N($C_m$-$C_n$alkyl)$_2$, —NH($C_3$-$C_n$cycloalkyl), —O—C(O)—$C_m$-$C_n$alkyl, —O—C(O)aryl, —OC(O)$C_3$-$C_n$cycloalkyl, —C(O)OH and —C(O)O$C_m$-$C_n$alkyl. It is generally preferred that the alkynyl group is unsubstituted, unless otherwise indicated.

The term "$C_m$-$C_n$haloalkyl" as used herein represents $C_m$-$C_n$alkyl wherein at least one C atom is substituted with a halogen (e.g. the $C_m$-$C_n$haloalkyl group may contain one to three halogen atoms), preferably chloro or fluoro. Typical haloalkyl groups are $C_1$-$C_2$haloalkyl, in which halo suitably represents fluoro. Exemplary haloalkyl groups include fluoromethyl, difluoromethyl and trifluoromethyl.

The term "$C_m$-$C_n$hydroxyalkyl" as used herein represents $C_m$-$C_n$alkyl wherein at least one C atom is substituted with one hydroxy group. Typical $C_m$-$C_n$hydroxyalkyl groups are $C_m$-$C_n$alkyl wherein one C atom is substituted with one hydroxy group. Exemplary hydroxyalkyl groups include hydroxymethyl and hydroxyethyl.

The term "Me" means methyl, and "MeO" means methoxy.

The term "$C_m$-$C_n$alkylcarbonyl" represents a radical of the formula $C_m$-$C_n$alkylC(=O)— wherein the $C_m$-$C_n$alkyl moiety is as defined above. Typically, "$C_m$-$C_n$alkylcarbonyl" is $C_1$-$C_6$alkylC(=O)—.

"$C_m$-$C_n$alkoxy" represents a radical $C_m$-$C_n$alkyl-O— wherein $C_m$-$C_n$alkyl is as defined above. Of particular interest is $C_1$-$C_4$alkoxy which includes methoxy, ethoxy, n-propoxy, isopropoxy, tert-butoxy, n-butoxy and isobutoxy. Methoxy and isopropoxy are typically preferred. $C_1$-$C_6$alkoxy has a corresponding meaning, expanded to include all straight and branched chain isomers of pentoxy and hexoxy.

The term "halo" represents a halogen radical such as fluoro, chloro, bromo or iodo. Typically, halo groups are chloro and especially fluoro.

The term "$C_3$-$C_n$cycloalkyl" represents a cyclic monovalent alkyl radical having the number of carbon atoms indicated, e.g. $C_3$-$C_7$cycloalkyl means a cyclic monovalent alkyl radical having from 3 to 7 carbon atoms. Preferred cycloalkyl radicals for use in the present invention are $C_3$-$C_4$alkyl i.e. cyclopropyl and cyclobutyl. A cycloalkyl group may be unsubstituted or substituted by one or more substituents which may be the same or different, each substituent being independently selected from the group consisting of halo, $C_2$-$C_n$alkenyl, $C_2$-$C_n$alkynyl, aryl, cycloalkyl, cyano, hydroxy, $C_m$-$C_n$alkoxy, aryloxy, $C_m$-$C_n$alkoxy$C_m$-$C_n$alkyl, $C_m$-$C_n$alkylthio, —$NH_2$, —NH($C_m$-$C_n$alkyl), —N($C_m$-$C_n$alkyl)$_2$, —NH(cycloalkyl), —O—C(O)$C_m$-$C_n$alkyl, —O—C(O)aryl, —O—C(O)$C_3$-$C_n$cycloalkyl, —C(O)OH and —C(O)Oalkyl. It is generally preferred that the cycloalkyl group is unsubstituted, unless otherwise indicated.

The term "$C_3$-$C_n$cycloalkenyl" represents a cyclic monovalent alkenyl radical having the number of carbon atoms indicated, e.g. $C_3$-$C_7$cycloalkenyl means a cyclic monovalent alkyl radical having from 3 to 7 carbon atoms, and including at least one unsaturated bond, typically one such bond. Preferred cycloalkenyl radicals for use in the present invention are $C_5$-$C_6$alkyl i.e. cyclopropenyl and cyclohexenyl. A cycloalkyl group may be unsubstituted or substituted by one or more substituents which may be the same or different, each substituent being independently selected from the group consisting of halo, alkenyl, alkynyl, aryl, cycloalkyl, cyano, hydroxy, alkoxy, aryloxy, alkoxyalkyl, alkylthio, —$NH_2$, —NH($C_m$-$C_n$alkyl), —N($C_m$-$C_n$alkyl)$_2$, —NH($C_3$-$C_n$cycloalkyl), —O—C(O)$C_m$-$C_n$alkyl, —O—C(O)aryl, —O—C(O)$C_3$-$C_n$cycloalkyl, —C(O)OH and —C(O)O$C_m$-$C_n$alkyl wherein $C_m$-$C_n$alkyl, $C_3$-$C_n$cycloalkyl and aryl are as defined above. It is generally preferred that the cycloalkyl group is unsubstituted, unless otherwise indicated.

The term "amino" represents $NH_2$.

Compounds of the invention can be prepared by the methods depicted in the schemes below and as detailed in the experimental descriptions. Starting materials and reagents used in the preparation of the compounds of the invention are available from commercial suppliers such as Aldrich Chemical Co., Bachem or Sigma, or they are prepared by methods known in the art following literature procedures. The schemes below are merely illustrative of some methods by which the compounds of the invention can be prepared, and various modifications to these schemes can be made and will be obvious to one skilled in the art.

A general route to compounds of the invention wherein $R^3$ is a bond with the adjacent carbon atom, thus providing a keto group, and $R^4$ is H is illustrated in Scheme 1.

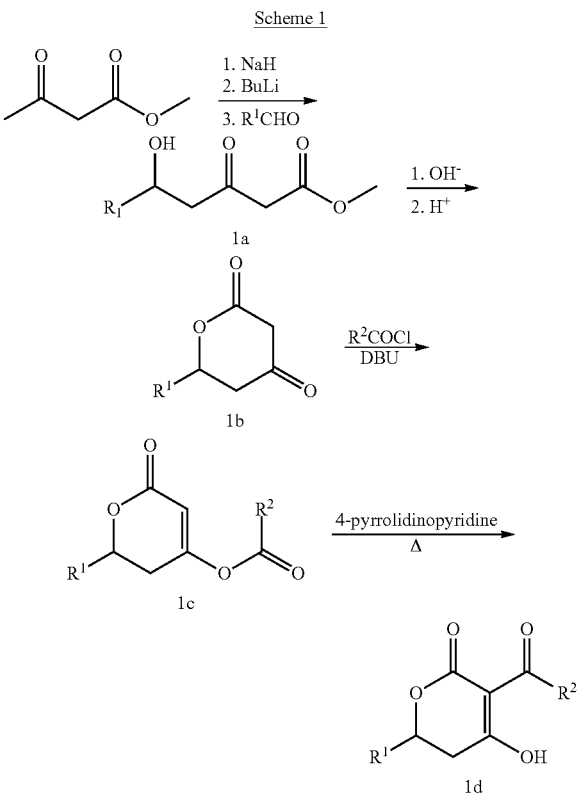

Scheme 1

Reaction of methyl acetoacetate with an aldehyde $R^1$CHO under basic conditions such as in the presence of sodium hydride and butyl lithium or similar provides the δ-hydroxy-β-keto ester (1a). The reaction is typically performed under anhydrous conditions in a solvent like THF or similar at a temperature below 5° C., such as between 0 and 5° C. Cyclisation of the afforded hydroxy compound effected by treatment with a base such as sodium hydroxide or similar followed by acidic treatment provides the pyran derivative (1 b). The O-substituent is then introduced by reaction with a desired acyl chloride $R^2COCl$ in the presence of a base such as DBU or similar, thus providing the ester derivative (1c). Treatment finally with a base like pyrrolidinopyridine or similar at an elevated temperature, such as between 100° C. and 150° C., preferably around 130° C., effects the rearrangement and provides the desired compound of formula I (1d).

Compounds of the invention wherein $R^3$ is a bond with the adjacent carbon atom, thus providing a keto group, and $R^4$ is optionally substituted $C_1$-$C_6$alkyl, $C_3$-$C_6$cycloalkyl or $C_3$-$C_6$cycloalkyl$C_1$-$C_3$alkyl are obtained by alkylation of the hydroxy group of compound 1d whereas compounds wherein $R^4$ is an ester or an amino acid ester, i.e. $C(O)R^5$ or $C(O)CHR^7NH_2$ respectively are achieved by acylation of the hydroxy group. These methods are generally illustrated in Scheme 2.

Scheme 2

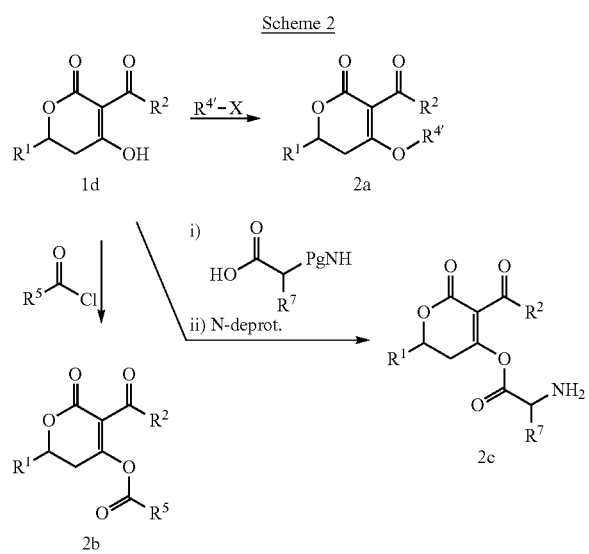

$R^{4'}$ is optionally substituted $C_1$-$C_6$alkyl, $C_3$-$C_6$cycloalkyl or $C_3$-$C_6$cycloalkyl$C_1$-$C_3$alkyl,
X is a leaving group or OH Alkylation of the hydroxy group of compound 1d effected by reaction with an alkylating agent like an dialkyl sulphate, an alkyl sulfonate such as a triflate, tosylate or mesylate or an alkyl halide of the desired alkyl group in the presence of a base such as sodium hydride or potassium carbonate or similar provides the alkylated derivative 2a. Alternatively, the group $R^{4'}$ may be introduced by reaction with the appropriate alcohol $R^{4'}$—OH in the presence of an acid like p-toluene sulfonic acid or equivalent typically at elevated temperature, or by using Mitsunobu conditions, i.e. in the presence of an azodicarboxylate such as DIAD or equivalent and triphenylphosphine.

Compounds of the invention wherein $OR^4$ is an ester group (2b), i.e. $R^4$ is a group of formula $C(O)R^5$ are obtained by acylation of alcohol 1e with an acylating agent such as an alkyl anhydride in the presence of pyridine, or an acid chloride or the like, whereas compounds wherein $OR^4$ is an amino acid ester group (2c), i.e. $R^4$ is a group of formula $C(O)CHR^7$ are obtained by reaction of the alcohol (1d) with an amino acid, optionally N-protected with a suitable N-protecting group such as a Boc, CBz or Fmoc group, in the presence of a suitable peptide coupling reagent such as EDAC or the like.

Compounds of the invention wherein $R^3$ is H are obtained by reduction of the exocyclic keto function using reduction conditions such sodium borohydride in the presence of cerium chloride in a solvent like THF or MeOH or similar, as illustrated in Scheme 3.

Scheme 3

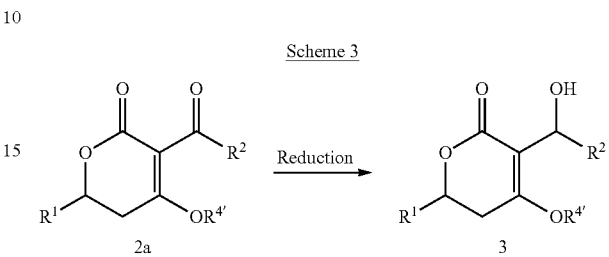

A route to compounds of the invention wherein $R^3$ is optionally substituted $C_1$-$C_6$alkyl, $C_3$-$C_6$cycloalkyl or $C_3$-$C_6$cycloalkyl$C_1$-$C_3$alkyl are obtained by alkylation of the hydroxy group of compound 3 whereas compounds wherein $R^3$ is an ester or an amino acid ester, i.e. $C(O)R^5$ or $C(O)CHR^7NH_2$ respectively are obtained by acylation of the hydroxy group. These routes are depicted in Scheme 4.

Scheme 4

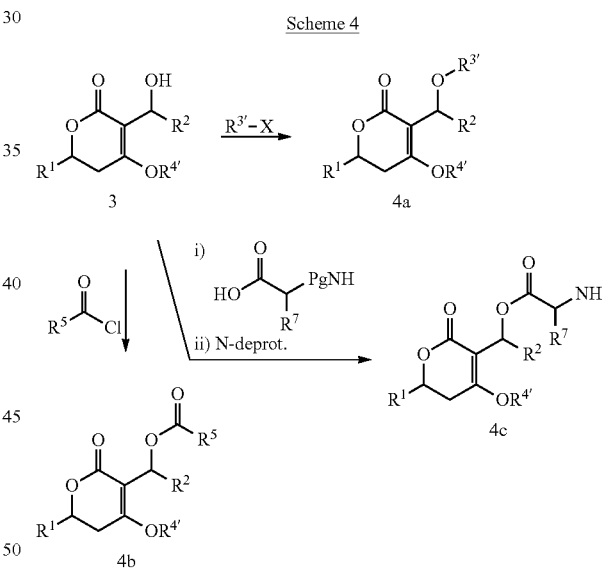

$R^{3'}$ and $R^{4'}$ are each independently optionally substituted $C_1$-$C_6$alkyl, $C_3$-$C_6$cycloalkyl or $C_3$-$C_6$cycloalkyl$C_1$-$C_3$alkyl
X is a leaving group or OH Alkylation of the hydroxy group of compound 3 effected by reaction with an alkylating agent like an dialkyl sulphate, an alkyl sulfonate such as a triflate, tosylate or mesylate or an alkyl halide of the desired alkyl group in the presence of a base such as sodium hydride or potassium carbonate or similar provides the alkylated derivative 4a. Alternatively, the group $R^{3'}$ may be introduced by reaction with the appropriate alcohol $R^{3'}$—OH in the presence of an acid like p-toluene sulfonic acid or equivalent typically at elevated temperature. Compounds of the invention wherein $OR^3$ is an ester group, i.e. $R^3$ is a group of formula $C(O)R^5$ are obtained by acylation of alcohol 3 with an acylating agent such as an alkyl anhydride in the presence of pyridine, or an acid chloride or the like, whereas compounds wherein OR³ is an amino acid ester group (4c), i.e. R³ is a group of formula C(O)CHR⁷NH₂ are obtained by reaction of the alcohol 3 with an amino acid, which is optionally N-protected with a suitable N-protecting group such as a Boc, CBz or Fmoc group, in the presence of a suitable peptide coupling reagent such as EDAC or the like.

To obtain compounds of formula I wherein R⁴ is H, and R³ together with the oxygen atom to which it is attached form an ether or acyloxy moiety, a protecting strategy as illustrated in Scheme 5 can be used.

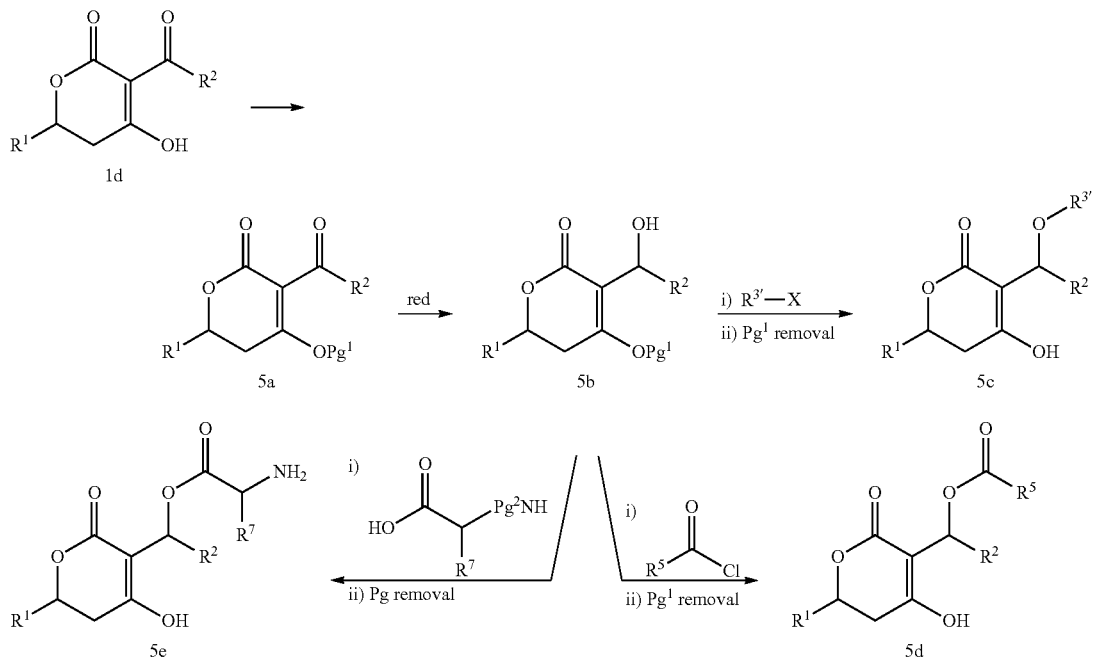

Scheme 5

R³' is optionally substituted C₁-C₆alkyl, C₃-C₆cycloalkyl or C₃-C₆cycloalkylC₁-C₃alkyl,
X is a leaving group or OH Protection of the hydroxy group of compound 1d as for instance an ether such as a THP ether or a trityl ether or the like or as a silyl ether such as tert.butyl dimethylsilyl or tert.butyl diphenylsilyl or similar provides protected derivative 5a. Reduction of the keto group to an alcohol can then be effected using e.g. sodium borohydride in the presence of cerium chloride in a solvent like THF or MeOH or similar conditions provide the exocyclic alcohol 5b. Alkylation or acylation using the desired alkylating or acylating agent respectively using conditions as described above followed by removal of the protecting group(s), then provides the O-substituted compounds 5c, 5d and 5e.

The pharmaceutical or veterinary compositions of the invention may be formulated in conventional manner, together with other pharmaceutically acceptable excipients if desired, into forms suitable for oral, parenteral, or topical administration. The modes of administration may include parenteral, for example, intramuscular, subcutaneous and intravenous administration, oral administration, topical administration and direct administration to sites of infection such as intraocular, intraaural, intrauterine, intranasal, intramammary, intraperitoneal, intralesional, etc.

The pharmaceutical or veterinary compositions of the invention may be formulated for oral administration. Traditional inactive ingredients may be added to provide desirable colour, taste, stability, buffering capacity, dispersion, or other known desirable features. Examples include red iron oxide, silica gel, sodium laurel sulphate, titanium dioxide, edible white ink, and the like. Conventional diluents may be used to make compressed tablets. Both tablets and capsules may be manufactured as sustained-release compositions for the continual release of medication over a period of time. Compressed tablets may be in the form of sugar coated or film coated tablets, or enteric-coated tablets for selective disintegration in the gastrointestinal tract. Liquid dosage forms for oral administration may contain colouring and/or flavouring to increase patient compliance. As an example, the oral formulation comprising compounds of the invention may be a tablet comprising any one, or a combination of, the following excipients: calcium hydrogen phosphate dehydrate, microcrystalline cellulose, lactose, hydroxypropyl methyl cellulose, and talc.

The compositions described herein may be in the form of a liquid formulation. Examples of preferred liquid compositions include solutions, emulsions, injection solutions, solutions contained in capsules. The liquid formulation may comprise a solution that includes a therapeutic agent dissolved in a solvent. Generally, any solvent that has the desired effect may be used in which the therapeutic agent dissolves and which can be administered to a subject. Generally, any concentration of therapeutic agent that has the desired effect can be used. The formulation in some variations is a solution which is unsaturated, a saturated or a supersaturated solution. The solvent may be a pure solvent or may be a mixture of liquid solvent components. In some variations the solution formed is an in situ gelling formulation. Solvents and types of solutions that may be used are well known to those versed in such drug delivery technologies.

The composition described herein may be in the form of a liquid suspension. The liquid suspensions may be prepared according to standard procedures known in the art. Examples of liquid suspensions include micro-emulsions, the formation of complexing compounds, and stabilising suspensions. The liquid suspension may be in undiluted or concentrated form. Liquid suspensions for oral use may contain suitable preservatives, antioxidants, and other excipients known in the art functioning as one or more of dispersion agents, suspending agents, thickening agents, emulsifying agents, wetting agents, solubilising agents, stabilising agents, flavouring and sweetening agents, colouring agents, and the like. The liquid suspension may contain glycerol and water.

The composition described herein may be in the form of an oral paste. The oral paste may be prepared according to standard procedures known in the art.

The composition described herein may be in the form of a liquid formulation for injection, such as intra-muscular injection, and prepared using methods known in the art. For example, the liquid formulation may contain polyvinylpyrrolidone K30 and water.

The composition described herein may be in the form of topical preparations. The topical preparation may be in the form of a lotion or cream, prepared using methods known in the art. For example, a lotion may be formulated with an aqueous or oily base and may include one or more excipients known in the art, functioning as viscosity enhancers, emulsifying agents, fragrances or perfumes, preservative agents, chelating agents, pH modifiers, antioxidants, and the like. For example, the topical formulation comprising one or more compounds of the invention may be a gel comprising anyone, or a combination of, the following excipients: PEG 8000, PEG 4000, PEG 200, glycerol, propylene glycol. The compound of formula I may further be formulated into a solid dispersion using SoluPlus (BASF, http://www.soluplus.com) and formulated with any one, or a combination of, the following excipients: PEG 8000, PEG 4000, PEG 200, glycerol, and propylene glycol.

For aerosol administration, the composition of the invention is provided in a finely divided form together with a non-toxic surfactant and a propellant. The surfactant is preferably soluble in the propellant. Such surfactants may include esters or partial esters of fatty acids.

The compositions of the invention may alternatively be formulated for delivery by injection. As an example, the compound is delivered by injection by any one of the following routes: intravenous, intramuscular, intradermal, intraperitoneal, and subcutaneous.

The compositions of the invention may alternatively be formulated using nanotechnology drug delivery techniques such as those known in the art. Nanotechnology-based drug delivery systems have the advantage of improving bioavailability, patient compliance and reducing side effects.

The formulation of the composition of the invention can include the preparation of nanoparticles in the form of nanosuspensions or nanoemulsions, based on compound solubility. Nanosuspensions are dispersions of nanosized drug particles prepared by bottom-up or top-down technology and stabilised with suitable excipients. This approach may be applied to the compounds of the invention which can have poor aqueous and lipid solubility, in order to enhance saturation solubility and improve dissolution characteristics. An example of this technique is set out in Sharma and Garg (2010) (Pure drug and polymer-based nanotechnologies for the improved solubility, stability, bioavailability, and targeting of anti-HIV drugs. Advanced Drug Delivery Reviews, 62: p. 491-502). Saturation solubility will be understood to be a compound-specific constant that depends on temperature, properties of the dissolution medium, and particle size (<1-2μιτι).

The composition of the invention may be provided in the form of a nanosuspension. For nanosuspensions, the increase in the surface area may lead to an increase in saturation solubility. Nanosuspensions are colloidal drug delivery systems, consisting of particles below 1μιη. Compositions of the invention may be in the form of nanosuspensions including nanocrystalline suspensions, solid lipid nanoparticles (SLNs), polymeric nanoparticles, nanocapsules, polymeric micelles and dendrimers. Nanosuspensions may be prepared using a top-down approach where larger particles may be reduced to nanometer dimensions by a variety of techniques known in the art including wet-milling and high-pressure homogenisation. Alternatively, nanosuspensions may be prepared using a bottom-up technique where controlled precipitation of particles may be carried out from solution.

The composition of the invention may be provided in the form of a nanoemulsion. Nanoemulsions are typically clear oil-in-water or water-in-oil biphasic systems, with a droplet size in the range of 100-500 nm, and with compounds of interest present in the hydrophobic phase. The preparation of nanoemulsions may improve the solubility of the compounds of the invention described herein, leading to better bioavailability. Nanosized suspensions may include agents for electrostatic or steric stabilisation such as polymers and surfactants. Compositions in the form of SLNs may comprise biodegradable lipids such as triglycerides, steroids, waxes and emulsifiers such as soybean lecithin, egg lecithin, and poloxamers. The preparation of a SLN preparation may involve dissolving/dispersing drug in melted lipid followed by hot or cold homogenisation. If hot homogenisation is used, the melted lipidic phase may be dispersed in an aqueous phase and an emulsion prepared. This may be solidified by cooling to achieve SLNs. If cold homogenisation is used, the lipidic phase may be solidified in liquid nitrogen and ground to micron size. The resulting powder may be subjected to high-pressure homogenisation in an aqueous surfactant solution.

The Compounds of Formula I as described herein may be dissolved in oils/liquid lipids and stabilised into an emulsion formulation. Nanoemulsions may be prepared using highland low-energy droplet reduction techniques. High-energy methods may include high-pressure homogenisation, ultrasonication and microfluidisation. If the low-energy method is used, solvent diffusion and phase inversion will generate a spontaneous nanoemulsion. Lipids used in nanoemulsions may be selected from the group comprising triglycerides, soybean oil, safflower oil, and sesame oil. Other components such as emulsifiers, antioxidants, pH modifiers and preservatives may also be added.

The composition may be in the form of a controlled-release formulation and may include a degradable or non-degradable polymer, hydrogel, organogel, or other physical construct that modifies the release of the compound. It is understood that such formulations may include additional inactive ingredients that are added to provide desirable colour, stability, buffering capacity, dispersion, or other known desirable features. Such formulations may further include liposomes, such as emulsions, foams, micelles, insoluble monolayers, liquid crystals, phospholipid dispersions, lamellar layers and the like. Liposomes for use in the invention may be formed from standard vesicle-forming lipids, generally including neutral and negatively charged phospholipids and a sterol, such as cholesterol. 100205] The formulations of the invention may have the advantage of increased solubility and/or stability of the compounds, particularly for those formulations prepared using nanotechnology techniques. Such increased stability and/or stability of the compounds of Formula I may improve bioavailability and enhance drug exposure for oral and/or parenteral dosage forms. Throughout this specification, unless the context requires otherwise, the word "comprise" or variations such as "comprises" or "comprising", will be understood to imply the inclusion of a stated integer or group of integers but not the exclusion of any other integer or group of integers.

In addition to the definitions above, the following abbreviations are used in the examples and synthetic schemes below. If an abbreviation used herein is not defined, it has its generally accepted meaning.

DBU 1,8-Diazabicyclo[5.4.0]undec-7-ene
DCM Dichloromethane
DMF N,N-Dimethylformamide
ES Electrospray
$Et_3N$ Triethylamine
EtOAc Ethyl acetate
EtOH Ethanol
LC Liquid chromatography
HOAc Acetic acid
HPLC High performance liquid chromatography
MeCN Acetonitrile
MeOH Methanol
MIC Minimum inhibition concentration
MS Mass spectrometry
PBS Phosphate buffered saline
Pg Protecting group
Ph Phenyl
THF Tetrahydrofuran
TFA Trifluoroacetic acid
VPB Vegetable Peptone Broth

SYNTHESIS EXAMPLES

Example 1

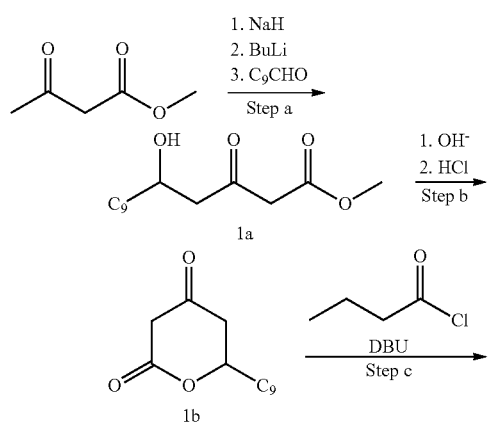

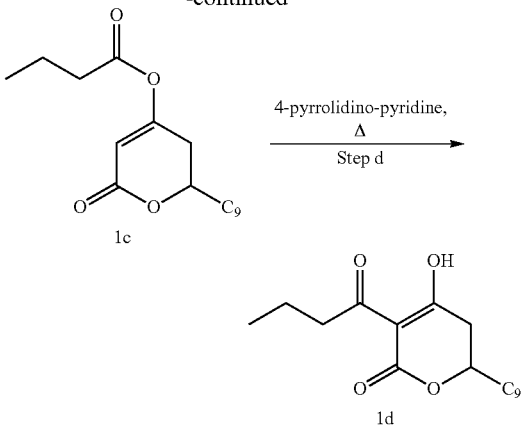

Step a) Methyl 5-hydroxy-3-oxotetradecanoate (1a)

Fresh NaH (60% dispersion in mineral oil, 0.88 g, 22 mmol) was added under nitrogen to THF (50 ml) and the suspension was cooled to 0° C. Methyl acetoacetate (2.16 ml, 20 mmol) was added drop wise while keeping the inside temp below 5° C. The stirring was continued at 0° C. for an additional 10 min, then 2.5 M n-BuLi (8.4 ml, 21 mmol) was added drop wise while keeping the inside temperature below 5° C. The stirring was continued for an additional 10 min, then, decanal (3.67 ml, 20 mmol) was added and the reaction mixture was stirred for an additional 30 min allowing the temperature to slowly increase to about 10° C. The reaction was quenched, with 6M HCl until acidic followed by addition of water and ether. The water phase was extracted twice with ether and the combined organic phases were carefully washed with brine to neutral pH and dried ($Na_2SO_4$). After filtration, the organic solvent was evaporated and a crude product (5.41 g) was obtained. The crude was recrystallized from n-hexanes and after standing at 5° C. a first crop of product (1.6 g) was obtained by transferring the mother liquid with a thin pipette at °0 C. A second crop (1.29 g) was obtained giving a total yield of 2.9 g (53%).

Step b) 6-Nonyldihydro-2H-pyran-2,4(3H)-dione (1b)

The compound from step a (1a, 1.61 g, 5.9 mmol) was mixed with 1M NaOH (15 ml). The reaction mixture was stirred at 0° C. for about 1 h, then 12M HCl (~3 ml) was added and the reaction mixture was allowed to attain room temperature overnight. Water (15 ml) was added and the mixture was extracted 3 times with DCM. The combined organic phases were washed with brine, dried ($Na_2SO_4$) and concentrated which gave crude title compound (1.26 g, 89%). The afforded crude product was taken to the next step without further purification.

Step c) 2-Nonyl-6-oxo-3,6-dihydro-2H-pyran-4-yl butyrate (1c)

The compound from step b (1b, 1.26 g, 5.24 mmol) was dissolved in toluene (15 ml) and DBU (1.18 ml, 7.86 mmol) was added. The reaction solution was cooled to 0° C. and butyryl chloride (0.82 ml, 7.86 mmol) was added drop wise. The reaction mixture was stirred at 0° C. for 1 h where after the temperature was allowed to reach room temperature.

After 3 hours, water was added and the reaction mixture was extracted twice with ether. The combined organic phases were washed with HCl solution, NaHCO$_3$ solution and brine. The organic phase was dried (Na$_2$SO$_4$) and concentrated. The afforded crude product was purified on a silica gel column eluted with hexanes/ether 3:1 which gave the title compound (1.18 g, 72.5%). LC-MS ES+311.07 [M+H]$^+$.

$^1$H NMR (400 MHz, CDCl$_3$) δ 7.25, 5.90, 5.89, 4.50, 4.49, 4.48, 4.47, 4.47, 4.46, 4.45, 4.44, 4.44, 4.43, 2.68, 2.68, 2.66, 2.65, 2.64, 2.64, 2.61, 2.61, 2.47, 2.45, 2.44, 2.43, 2.41, 2.40, 2.39, 2.35, 2.33, 2.31, 2.26, 2.24, 2.23, 2.22, 2.15, 1.86, 1.85, 1.84, 1.83, 1.83, 1.82, 1.81, 1.80, 1.80, 1.79, 1.79, 1.78, 1.77, 1.75, 1.73, 1.72, 1.70, 1.68, 1.66, 1.65, 1.64, 1.63, 1.63, 1.61, 1.60, 1.54, 1.52, 1.51, 1.49, 1.48, 1.48, 1.42, 1.41, 1.39, 1.38, 1.29, 1.28, 1.25, 1.01, 0.99, 0.97, 0.95, 0.93, 0.91, 0.89, 0.87, 0.86, 0.06, −0.01.

Step d) 3-Butyryl-6-nonyl-4-hydroxy-5,6-dihydro-2H-pyran-2-one (1d)

The compound from step c (1c, 2.5 g, 8.05 mmol) was dissolved in toluene (50 ml) and 4-pyrrolidinopyridine (60 mg, 0.4 mmol) was added. The reaction was heated at 130° C. for 4 hrs. The solvent was evaporated and the residue purified on a silica gel column eluted with ether/hexanes 1:5 which gave a crude product as a solid (1.89 g). The solid was recrystallized from 10 ml warm hexanes and stored at 5° C. for 3 days. The mother liquid was removed by a thin pipette at 0° C. The crystals were then washed with 1 ml cold hexane. The white crystals were dried in vacuum which gave the title compound (1.03 g, 41%). The purity was determined to 99% by LC/UV analysis. LC-MS ES+311.2 [M+H]$^+$.

$^1$H NMR (400 MHz, CDCl$_3$) δ 17.88, 16.18, 7.25, 4.47, 4.45, 4.43, 4.37, 4.36, 4.36, 4.36, 4.35, 4.35, 4.34, 4.34, 4.33, 4.33, 4.32, 4.32, 4.32, 4.31, 3.08, 3.06, 3.06, 3.04, 3.04, 3.03, 3.02, 3.02, 3.00, 2.99, 2.98, 2.98, 2.97, 2.97, 2.96, 2.94, 2.93, 2.92, 2.69, 2.66, 2.65, 2.62, 2.61, 2.60, 2.57, 2.56, 2.56, 2.55, 2.55, 2.23, 1.83, 1.81, 1.81, 1.80, 1.80, 1.79, 1.79, 1.78, 1.78, 1.77, 1.77, 1.77, 1.76, 1.76, 1.75, 1.74, 1.74, 1.72, 1.71, 1.71, 1.69, 1.69, 1.69, 1.67, 1.67, 1.65, 1.65, 1.64, 1.63, 1.63, 1.62, 1.62, 1.61, 1.59, 1.58, 1.56, 1.53, 1.51, 1.50, 1.50, 1.48, 1.48, 1.47, 1.47, 1.46, 1.45, 1.44, 1.42, 1.41, 1.39, 1.38, 1.37, 1.32, 1.31, 1.28, 1.25, 1.02, 1.00, 0.98, 0.96, 0.88, 0.87, 0.85, −0.02.

Example 2A & 2B Separation of the Enantiomers of Compound 1d

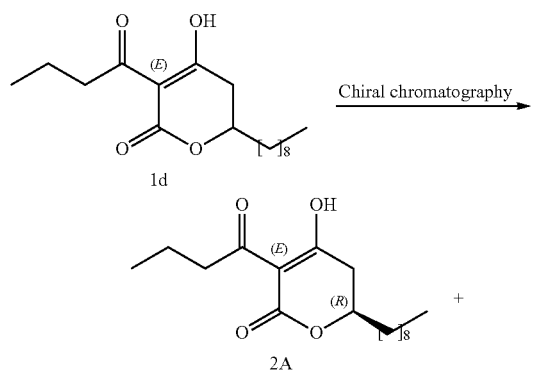

Compound 1d (100 mg) was resolved by chiral chromatography using a Lux Cell-3 column eluted with A=hexane, B=80% hexane, 20% EtOH+1% TFA. The enantiomeric purity was determined by an analytical Lux Cell-3 column and the absolute configuration was postulated based on related Podoblastins cf. *J. Pesticide Sci.* 13, 605-613 (1988).

Peak 1—Compound 2A:
Amount 44 mg, enantiomeric purity 99.9%, [α]$_D$−31 (c=0.245, DCM), absolute configuration (6R)

Peak 2—Compound 2B:
Amount 38 mg, enantiomeric purity 99.8%, [α]D+33° (c=0.24, DCM), absolute configuration (6S).

Example 29, Acylation of Compound 1d

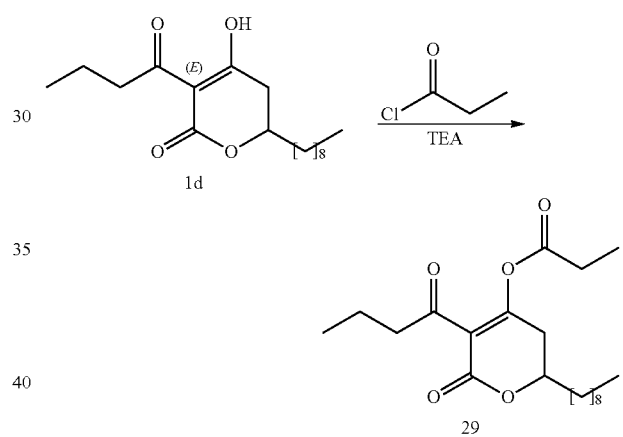

5-Butyryl-2-nonyl-6-oxo-3,6-dihydro-2H-pyran-4-yl propionate (29)

Propionyl chloride (0.013 mL, 0.150 mmol) was added at 0° C. to a solution of compound 1d (31.0 mg, 0.100 mmol) in ACN (3.00 mL) and TEA (0.021 mL, 0.150 mmol). The reaction mixture was left at room temperature and stirred for 18 h. DCM was added and the solution was washed with water. The organic layer was dried (Na$_2$SO$_4$), filtered and concentrated, which gave the title compound.

Compound 3 to 28 listed in Table 1 below were prepared according to the method described in Example 1. $^1$H NMR was ran for the penultimate and last step for Compounds 2-28 and the spectra were found to be in accordance with the spectra for compounds 1c and 1d.

BIOLOGICAL EXAMPLES

Biological Example 1—Determination of Minimum Inhibitory Concentration (MIC) Against Gram-Positive and Gram-Negative Pathogens At first (Table 1), MIC is determined by broth microdilution method. The test medium is Antibiotic Medium 3

(AM3; Difco Ltd) mixed with Phosphate Buffered Saline (PBS) in proportions 1:1. Selected MIC values are verified using cation-adjusted Mueller Hinton Broth (MHB; BD). Cell concentration of tested pathogen is adjusted to between 3 and $5 \times 10^5$ cells per ml. To verify cell concentration of tested pathogen, viable cell counts are performed directly after each MIC-test by dilution method with PBS as a dilution solvent. Cells are counted on the agar plates with 50% strength Vegetable Peptone Broth (50% VPB; Oxoid Ltd) after 16 to 20 h of incubation at 37° C.

In order to establish MIC, appropriate volumes of solutions of test compounds (100, 10, 1 and if needed 0.1 μg/ml) dissolved in MeOH are dispensed into wells of 96-wells microtiter plates and the solvent is evaporated. MIC of the test compounds is detected in a concentration range between 0.05 and 20 μg per ml. Cells of pathogen suspended in test medium are distributed to the wells and the plates are incubated for 16 to 20 h at 37° C. Negative controls are wells with the test medium only and positive controls are wells with the pathogen in test medium. The MIC is defined as the lowest concentration of each compound with no visible growth of pathogen.

Example compounds of formula I were examined for antibacterial activity against the Gram-positive bacterium *Staphylococcus aureus* strain LMG15975 using the above described method (Table 1).

MIC of Example 1 and its selected derivatives (Ex. 14, Ex. 16 and Ex. 17) (Table 5) is, additionally, determined using the broth micro-dilution method according to M07-A9 Clinical and Laboratory Standards Institute (CLSI) guidelines. All pathogens are tested according to M07-A9 and M26 CLSI guidelines using the appropriate broth medium. Negative controls (lack of bacterial cells) and growth control are included in the plates. *S. aureus* ATCC 29213 and *S. pneumoniae* ATCC49619 are evaluated as assay quality control strain. The MIC is defined as the lowest concentration of each compound with no visible growth of pathogen. The MIC of Example 1 is compared to the MIC of ciprofloxacin (Table 6).

Antibacterial activity of the tested compounds determined as MIC is summarized in Tables 1-7.

TABLE 1

| Compound | $R^1$ | $R^2$ | MS [M + H]$^+$ | MIC (μg/ml) | MIC (μM) | $CC_{50}$ (μg/mL) |
|---|---|---|---|---|---|---|
| Ex. 1 | nonyl | Propyl | 311.2 | 0.8 | 2.5 | 33 |
| Ex. 2A | nonyl | Propyl | 311.2 | 1-2 | 3.2-6.4 | 27 |
| Ex. 2B | nonyl | Propyl | 311.2 | 0.4-0.6 | 1.3-1.9 | 25 |
| Ex. 3 | decyl | Butyl | 339.2 | 0.4-0.6 | 1.2-1.8 | 13 |
| Ex. 4 | 1-trans-nonenyl | Propyl | 309.33 | 0.8-1.2 | 2.6-3.9 | 36 |
| Ex. 5 | nonyl | Ethyl | 297.4 | 0.65 | 2.2 | 50 |
| Ex. 6 | octyl | Ethyl | 283.3 | 1.2 | 4.3 | 55 |
| Ex. 7 | octyl | methyl | 269.3 | 2.5 | 9.3 | 65 |
| Ex. 8 | nonyl | Butyl | 325.4 | ≤0.6 | ≤1.9 | 36 |
| Ex. 9 | nonyl | methyl | 283.3 | 1.5-2.5 | 2.1-4.3 | 71 |
| Ex. 10 | decyl | Ethyl | 311.4 | 0.4-0.8 | 1.3-2.6 | 60 |
| Ex. 11 | decyl | methyl | 297.2 | 0.8-1.2 | 2.7-4.0 | 40 |
| Ex. 12 | decyl | Propyl | 325.2 | 0.6-0.8 | 1.9-2.6 | 25 |
| Ex. 13 | octyl | propyl | 297.2 | 0.8-1.5 | 2.7-5.1 | 30 |
| Ex. 14 | nonyl | cyclohexyl-methyl | 365.3 | 0.25 | ≤0.3 | 14 |
| Ex. 15 | nonyl | isobutyl | 325.2 | 0.2-0.4 | 0.6-1.2 | 21 |
| Ex. 16 | undecyl | propyl | 339.2 | 0.1-0.2 | 0.3-0.6 | 19 |
| Ex. 17 | undecyl | butyl | 353.2 | 0.1-0.2 | 0.3-0.6 | 12 |
| Ex. 18 | nonyl | pentyl | 339.3 | 0.6-0.8 | 1.8-2.4 | 15 |
| Ex. 19 | 7-cyanoheptyl | propyl | 308.1 | 40-50 | 133-166 | >100 |
| Ex. 20 | 7-methoxy-heptyl | propyl | 313.1 | 20-30 | 64-96 | 80 |
| Ex. 21 | 2,6-dimethyl-hept-5-enyl | propyl | 309.2 | 2-3 | 6.5-9.7 | na |
| Ex. 22 | cyclopentyl-methyl | propyl | 267.2 | 6-12 | 22-45 | na |
| Ex. 23 | 6-methoxy-hexyl | cyclopentyl-methyl | 339.2 | 10-20 | 29-59 | na |
| Ex. 24 | nonyl | 2-methoxy-ethyl | 327.2 | 2-5 | 6.1-15 | na |
| Ex. 25 | 6-methoxy-hexyl | cyclopropyl-methyl | 311.2 | >20 | >64 | na |
| Ex. 26 | nonyl | (tetrahydro-2H-pyran-4-yl)methyl | 367.2 | 0.5-1 | 1.4-2.7 | na |
| Ex. 27 | 7-cyanoheptyl | (tetrahydro-2H-pyran-4-yl)methyl | 364.2 | 2-5 | 5.5-14 | na |
| Ex. 28 | 7-cyanoheptyl | cyclohexyl-methyl | 362.2 | >20 | >55 | na |
| Test comp. | ethyl | propyl | 213.0 | >50 | >240 | >100 | na = not available

TABLE 2

Activity for selected compounds, with increasing lengths of $R_1$ or $R_2$, towards *A. baumannii* (G−) and *S. aureus* (G+).

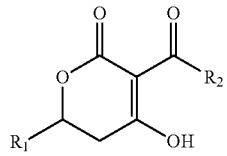

| Compound | $R_1$ | $R_2$ | MIC (µg/ml) *A. baumannii* | MIC (µg/ml) *S. aureus* |
|---|---|---|---|---|
| Ex. 9 | nonyl | methyl | >64 | 1.5-2.5 |
| Ex. 5 | nonyl | ethyl | 32-48 | 0.7 |
| Ex. 1 | nonyl | propyl | 16-24 | 0.8 |
| Ex. 8 | nonyl | butyl | 8-16 | <0.6 |
| Ex. 18 | nonyl | pentyl | 4-8 | 0.6-0.8 |
| Comp. Ex. | ethyl | propyl | >64 | >50 |
| Nat. prod.* | heptyl | propyl | >64 | 1-2 |
| Ex. 13 | octyl | propyl | 24-32 | 0.8-1.5 |
| Ex. 1 | nonyl | propyl | 8-16 | 0.8 |
| Ex. 12 | decyl | propyl | 8-16 | 0.6-0.8 |
| Ex. 16 | undecyl | propyl | <4 | 0.1-0.2 |

*The compound was isolated from cultures of a soil bacterium.

TABLE 3

Sensitivity of 4 mupirocin-resistant strains of *Staphylococcus aureus* against selected example compounds (Table 1). All strains had MIC values above 256 ug/ml for mupirocin.

| Isolate | MIC (µg/ml) | | | |
|---|---|---|---|---|
| | Ex. 1 | Ex. 8 | Ex. 14 | Ex. 24 |
| *S. aureus* V55 | ≤0.1 | ≤0.1 | ≤0.1 | >1 ≤ 2 |
| *S. aureus* V86 | >0.1 ≤ 0.25 | ≤0.1 | ≤0.1 | >1 ≤ 2 |
| *S. aureus* V308 | >0.1 ≤ 0.25 | >0.1 ≤ 0.25 | ≤0.1 | >1 ≤ 2 |
| *S. aureus* V321 | >0.1 ≤ 0.25 | ≤0.1 | ≤0.1 | >1 ≤ 2 |

TABLE 4

Sensitivity of *Staphylococcus aureus*, *Mycobacterium smegmatis*, *M. frederiksbergense* and *Bacillus cereus*, against selected example compounds (Table 1)

| Compound | MIC (µg/ml) | | | |
|---|---|---|---|---|
| | *S. aureus* | *M. smegmatis* | *M. frederiksbergense* | *B. cereus* |
| Ex. 1 | 0.8 | >0.5 ≤ 1 | ≤0.5 | ≤1 |
| Ex. 5 | 0.7 | >0.5 ≤ 1 | >1 ≤ 2 | ≤1 |
| Ex. 8 | ≤0.6 | ≤4 | ≤4 | ≤1 |
| Ex. 10 | >0.4 ≤ 0.8 | >1 ≤ 2 | ≤0.5 | ≤1 |
| Ex. 14 | ≤0.1 | >1 ≤ 2 | >0.5 ≤ 1 | ≤1 |
| Ex. 17 | >0.1 ≤ 0.2 | >1 ≤ 2 | >0.5 ≤ 1 | ≤1 |
| Ex. 23 | >10 ≤ 20 | >4 ≤ 8 | >8 ≤ 16 | >4 ≤ 8 |

TABLE 5

Antimicrobial Susceptibility Test (AST) by Broth Microdilution Method according to M07-A9 CLSI guidelines. The tested compounds are Example 14, 16, 17 and 1 (Table 1)

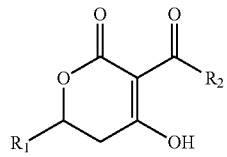

| Organism | Main phenotype of antibiotic resistance | MIC (µg/mL) | | | |
|---|---|---|---|---|---|
| | | Ex. 14 | Ex. 16 | Ex. 17 | Ex. 1 |
| S. aureus ATCC29213 | QC strain | 2 | 4 | 16 | 4 |
| S. aureus MO17 | Methicillin-sensitive | 1 | 4 | 4 | 2 |
| S. aureus PICI | Methicillin-resistant | 1 | 4 | 8 | 4 |
| S. aureus 7280 | Methicillin-resistant | 2 | 8 | 8 | NT |
| S. epidermis RO7 | Methicillin-sensitive | 0.5 | 0.5 | 0.5 | 1 |
| S. epidermis Staph 1 | Methicillin-resistant | 0.5 | 0.5 | 0.5 | NT |
| S. epidermis TA12 | Methicillin-resistant | 0.5 | 1 | 0.5 | 2 |
| E. faecium 7 | Vancomycin-resistant | 1 | 2 | 1 | 2 |
| E. faecalis 24 | Vancomycin-sensitive | 1 | 1 | 1 | 2 |
| E. faecalis 14 | Vancomycin-resistant | 1 | 1 | 1 | NT |
| S. aureus LMG 15975 (SLU) | Methicillin-resistant | 0.25 | 0.1-0.2 | 0.1-0.2 | 0.8 |
| S. aureus 4384 (SSI) | Methicillin-resistant | NT | NT | NT | 2 |
| $CC_{50}$ (µg/mL) | | 14 | 19 | 12 | 38 |

TABLE 6

Antimicrobial Susceptibility Test (AST) by Broth Microdilution Method according to M07-A9 CLSI guidelines. The tested compound is Example 1, $R^1$ = nonyl, R2 = propyl, in comparison to Ciprofloxacin

| Organism | Main Phenotype of Antibiotic Resistance | MIC (µg/mL) | |
|---|---|---|---|
| | | Ex 1 | Ciprofloxacin |
| S. aureus ATCC 29213 | QC strain | 4 | 0.125 |
| S. aureus 4216 | Tetracycline-resistant | 2 | >32 |
| S. aureus 853E | Macrolide-sensitive | 2 | 0.25 |
| S. aureus 6 Holland | Macrolide-resistant (M) | 1 | 1 |
| S. aureus 56 Japan | Macrolide-resistant (MLSi) | 4 | >8 |
| S. aureus PK2 | Macrolide-resistant (MLSc) | 2 | 0.25 |
| S. aureus MO 17 | MSSA | 2 | 0.5 |
| S. aureus PICI | MRSA | 4 | >32 |
| S. aureus FR 131 | Quinolone-resistant | 2 | >32 |
| S. pneumoniae ATCC 49619 | QC strain | 4 | 0.5 |
| S. pneumoniae 158bg | Macrolide-resistant (M) | 4 | 2 |
| S. pneumoniae SP030 | Macrolide- sensitive | 8 | 0.5 |
| S. pneumoniae 956 | Macrolide-resistant (MLSc) | 4 | 1 |
| S. pneumoniae 19A-TN | Quinolone-sensitive | 8 | 0.5 |
| S. pneumoniae TE 122-024 | Quinolone-resistant | 8 | 2 |
| S. pneumoniae TE 122-026 | Tetracycline-resistant | 4 | 1 |
| S. pneumoniae BAA1407 | Macrolide-resistant (M + MLS) | 8 | 1 |
| S. pyogenes 21 Finland | Macrolide-resistant (MLSc) | 8 | 0.25 |
| S. pyogenes 2 Finland | Macrolide-resistant (M) | 8 | 5 |
| S. pyogenes 29A-TF | Macrolide- sensitive | 8 | 0.25 |
| S. epidermidis RO7 | MSSE | 1 | 0.125 |
| S. epidermidis TA12 | MRSE | 2 | >32 |
| E. faecalis E.cocco 24 | Vancomycin -sensitive | 2 | 0.5 |
| E. faecalis E.cocco 12 | Vancomycin -resistant | 2 | 32 |
| E. faecium E.coc 7 | Vancomycin -resistant | 2 | >32 |

TABLE 7

Table 7 shows results for Example 14) and Example 1 tested against a panel of Gram-negative bacteria.

|  |  |  |  | µg/mL | |
| --- | --- | --- | --- | --- | --- |
| EN no. | Species |  | Other ID | Ex. 14 | Ex. 1 |
| *Wide range of Gram-negative species* | | | | | |
| EN0454 | *Serratia marescens* | G− | PKL 3692 | >64 | >64 |
| EN0455 | *Micrococcus luteus* | G+ | PKL 3693 | 0.5 | 0.5 |
| EN0457 | *Proteus mirabilis* | G− | PKL 3695 | >64 | >64 |
| EN0458 | *E. coli* B | G− | PKL 3698 | >64 | >64 |
| EN0459 | *P. aeruginosa* | G− | PKL 3699 | >64 | >64 |
| EN0460 | *P. aeruginosa* | G− | PKL 3704 | >64 | >64 |
| EN0461 | *Enterobacter aerogenes* | G− | PKL 3706 | >64 | >64 |
| EN0456 | *S. epidermidis* | G+ | PKL 3694 | 1 | 1 |
| EN0465 | *Citrobacter* sp. | G− | PKL 3710 | >64 | >64 |
| EN0466 | *S. typhimurium* | G− | TH6509 | >64 | >64 |
| EN0180 | *A. Pittii/nosocomialis* | G− |  | >64 | >64 |
| EN0392 | *K. oxytoca* | G− |  | >64 | >64 |
| EN0422 | *P. aeruginosa* | G− |  | >64 | >64 |
| EN0445 | *P. mirabilis* ST19 | G− |  | >64 | >64 |
| *ENABLE Primary MIC panel strains* | | | | | |
| EN001 | *E. coli* | G− | WT | >64 | >64 |
| EN002 | *E. coli* | G− | DtolC | >64 | 4 |
| EN003 | *E. coli* | G− | D22 (lps mut) | >64 | >64 |
| EN004 | *P. aeruginosa* | G− | WT | >64 | >64 |
| EN005 | *P. aeruginosa* | G− | Efflux mut | >64 | 2 |
| EN006 | *K. pneumoniae* | G− | WT | >64 | >64 |
| EN007 | *A. baumanii* | G− | WT | >64 | >64 |
| EN008 | *S. aureus* | G+ | Gram+ | 2 | 2 |
| *ENABLE L2C MIC panel strains (isogenic efflux pairs)* | | | | | |
| EN0010 | *K. pneumoniae* | G− |  | >64 | >64 |
| EN0011 | *K. pneumoniae* | G− | Efflux mut | >64 | 8 |
| EN0012 | *E. coli* | G− |  | >64 | >64 |
| EN0013 | *E. coli* | G− | Del-tolC | 16 | 0.5 |
| EN0014 | *P. aeruginosa* | G− |  | >64 | >64 |
| EN0015 | *P. aeruginosa* | G− | Efflux mut | >64 | >64 |
| EN0016 | *A. baumanii* | G− |  | >64 | >64 |
| EN0017 | *A. baumanii* | G− | Efflux mut | >64 | >64 |

Cytotoxicity Assay

Cytotoxicity of the compounds was evaluated in HepG2 cells as follows: HepG2 (ATCC cat. no. HB-8065) hepatocellular carcinoma cells were maintained in Dulbecco's Modified Eagle Medium supplemented with 10% heat inactivated fetal calf serum, penicillin (50 U/ml) and streptomycin (50 µg/ml). Briefly, cells were passaged into 96 well microplates ($1 \times 10^4$ cells/well) and the next day, test compounds were added in two-fold serial dilutions starting from a final top concentration of 100 µM. After another 48 hours of incubation at 37°, the number of viable cells in each well was assessed by using a water-soluble tetrazolium salt, WST-8 assay (cell counting Kit-8 from Dojindo). The concentration causing 50% decrease in cell viability ($CC_{50}$) was determined.

Biological Example 2, In Vivo Pharmacokinetics

Compound Example 1_(Table 1) was administered orally to triplicate mice in a conventional 20% HPBCD vehicle. Two doses were administered, 10 and 50 µmol/kg. Blood samples were taken at relevant timepoints over 48 hours, as depicted in the Table 8 below, and the plasma concentration of Example 1 determined by LC/MS/MS. The compound exhibited excellent dose dependent exposure. Macroscopic examination of the animals and their behaviour did not show any sign of adverse effect.

TABLE 8

Determination of Example 1 concentration in mouse plasma following oral administration of Example 1 (50 µmol/kg) in a 20% HPBCD vehicle. Concentrations were determined at the indicated times using LC/MS/MS.

| | Concentration in plasma (µM) | | |
| --- | --- | --- | --- |
| Time (h) | Mouse 1 | Mouse 2 | Mouse 3 |
| 0.25 | 73 | 71 | 162 |
| 0.5 | 101 | 126 | 163 |
| 1 | 136 | 178 | 217 |
| 3 | 204 | 234 | 246 |
| 5 | 213 | 294 | 320 |
| 7 | 266 | 240 | 280 |
| 24 | 169 | 152 | 94 |
| 48 | 17 | 11 | 15 |

Biological Example 3, In Vitro Absorption

Permeability

This experiment measures transport of inhibitors through the cells of the human gastroenteric canal. The assay uses the well-known Caco-2 cells with a passage number between 40 and 60.

Apical to Basolateral Transport

Generally every compound will be tested in 2-4 wells. The basolateral and the apical wells will contain 1.5 mL and 0.4 mL transport buffer (TB), respectively, and the standard concentration of the tested substances is 10 µM. Furthermore all test solutions and buffers will contain 1% DMSO. Prior to the experiment the transport plates are pre-coated with culture medium containing 10% serum for 30 minutes to avoid nonspecific binding to plastic material. After 21 to 28 days in culture on filter supports, the cells are ready for permeability experiments.

Transport plate no 1 comprises 3 rows of 4 wells each. Row 1 is denoted Wash, row 2 "30 minutes" and row 3 "60 minutes". Transport plate no 2 comprises 3 rows of 4 wells, one denoted row 4 "90 minutes", row 5 "120 minutes and the remaining row unassigned.

The culture medium from the apical wells is removed and the inserts are transferred to a wash row (No. 1) in a transport plate (plate no.1) out of 2 plates without inserts, which have already been prepared with 1.5 mL transport buffer (HBSS, 25 mM HEPES, pH 7.4) in rows 1 to 5. In A→B screening the TB in basolateral well also contains 1% Bovine Serum Albumin.

0.5 mL transport buffer (HBSS, 25 mM MES, pH 6.5) is added to the inserts and the cell monolayers equilibrated in the transport buffer system for 30 minutes at 37° C. in a polymix shaker. After being equilibrated to the buffer system the Transepithelial electrical resistance value (TEER) is measured in each well by an EVOM chop stick instrument. The TEER values are usually between 400 to 1000Ω per well (depends on passage number used).

The transport buffer (TB, pH 6.5) is removed from the apical side and the insert is transferred to the 30 minutes row (No. 2) and fresh 425 µL TB (pH 6.5), including the test substance is added to the apical (donor) well. The plates are incubated in a polymix shaker at 37° C. with a low shaking velocity of approximately 150 to 300 rpm.

After 30 minutes incubation in row 2, the inserts are moved to new pre-warmed basolateral (receiver) wells every 30 minutes; row 3 (60 minutes), 4 (90 minutes) and 5 (120 minutes).

25 μL samples are taken from the apical solution after ~2 minutes and at the end of the experiment. These samples represent donor samples from the start and the end of the experiment.

300 μL will be taken from the basolateral (receiver) wells at each scheduled time point and the post value of TEER is measured at the end the experiment. To all collected samples acetonitrile will be added to a final concentration of 50% in the samples. The collected samples will be stored at −20° C. until analysis by HPLC or LC-MS.

Basolateral to Apical Transport

Generally every compound will be tested in 2-4 wells. The basolateral and the apical wells will contain 1.55 mL and 0.4 mL TB, respectively, and the standard concentration of the tested substances is 10 μM. Furthermore all test solutions and buffers will contain 1% DMSO. Prior to the experiment the transport plates are precoated with culture medium containing 10% serum for 30 minutes to avoid nonspecific binding to plastic material.

After 21 to 28 days in culture on filter supports the cells are ready for permeability experiments. The culture medium from the apical wells are removed and the inserts are transferred to a wash row (No. 1) in a new plate without inserts (Transport plate).

The transport plate comprises 3 rows of 4 wells. Row 1 is denoted "wash" and row 3 is the "experimental row". The transport plate has previously been prepared with 1.5 mL TB (pH 7.4) in wash row No. 1 and with 1.55 mL TB (pH 7.4), including the test substance, in experimental row No. 3 (donor side).

0.5 mL transport buffer (HBSS, 25 mM MES, pH 6.5) is added to the inserts in row No. 1 and the cell monolayers are equilibrated in the transport buffer system for 30 minutes, 37° C. in a polymix shaker. After being equilibrated to the buffer system the TEER value is measured in each well by an EVOM chop stick instrument.

The transport buffer (TB, pH 6.5) is removed from the apical side and the insert is transferred to row 3 and 400 μL fresh TB, pH 6.5 is added to the inserts. After 30 minutes 250 μL is withdrawn from the apical (receiver) well and replaced by fresh transport buffer. Thereafter 250 μL samples will be withdrawn and replaced by fresh transport buffer every 30 minutes until the end of the experiment at 120 minutes, and finally a post value of TEER is measured at the end of the experiment. A 25 μL samples will be taken from the basolateral (donor) compartment after ~2 minutes and at the end of the experiment. These samples represent donor samples from the start and the end of the experiment.

To all collected samples acetonitrile will be added to a final concentration of 50% in the samples. The collected samples will be stored at −20° C. until analysis by HPLC or LC-MS.

Calculation

Determination of the cumulative fraction absorbed, $FA_{cum}$, versus time. $FA_{cum}$ is calculated from:

$$FA_{cum} = \sum \frac{C_{Ri}}{C_{Di}}$$

Where $C_{Ri}$ is the receiver concentration at the end of the interval i and $C_{Di}$ is the donor concentration at the beginning of interval i. A linear relationship should be obtained.

The determination of permeability coefficients ($P_{app}$, cm/s) are calculated from:

$$P_{app} = \frac{(k \cdot V_R)}{(A \cdot 60)}$$

where k is the transport rate (min$^{-1}$) defined as the slope obtained by linear regression of cumulative fraction absorbed ($FA_{cum}$) as a function of time (min), $V_R$ is the volume in the receiver chamber (mL), and A is the area of the filter (cm$^2$).

TABLE 9

| Reference compounds | | |
|---|---|---|
| Category of absorption in man | Markers | absorption in man (%) |
| PASSIVE TRANSPORT | | |
| Low (0-20%) | Mannitol | 16 |
|  | Methotrexate | 20 |
| Moderate (21-75%) | Acyclovir | 30 |
| High (76-100%) | Propranolol | 90 |
|  | Caffeine | 100 |
| ACTIVE TRANSPORT | | |
| Amino acid transporter | L-Phenylalanine | 100 |
| ACTIVE EFFLUX | | |
| PGP-MDR1 | Digoxin | 30 |

Greater permeability through the gastrointestinal tissue is advantageous in that it allows for the use of a smaller dose to achieve similar levels of exposure to a less permeable compound administered in a higher dose. A low dose is advantageous in that it minimizes the cost of goods for a daily dose, which is a crucial parameter in a drug which is taken for protracted time periods.

The compound of Example 1 exhibited an excellent Caco2 permeability value of $P_{app}$ 53 cmsec$^{-1}$.

The invention claimed is:

1. A compound of Formula I:

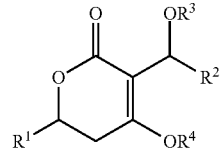

Formula I wherein

R$^1$ is substituted or unsubstituted C$_2$-C$_{20}$ alkenyl with 1-3 unsaturated bonds;

R$^2$ is selected from the group consisting of substituted or unsubstituted C$_1$-C$_{20}$ alkyl, C$_2$-C$_{20}$ alkenyl, C$_2$-C$_{20}$ alkynyl, C$_1$-C$_6$ alkoxy C$_1$-C$_3$ alkyl, cyclopropylmethyl, cyclobutylmethyl, cyclopentylmethyl and cyclohexylmethyl;

R$^3$ is H or a bond along with the adjacent carbon defining a keto group, R$^5$, C(O)R$^5$, CR$^a$R$^b$OR$^5$, CR$^a$R$^b$OC(O)R$^5$, CR$^a$R$^b$OC(O)OR$^5$ or C(O)CHR$^7$NH$_2$;

R$^4$ is R$^5$, C(O)R$^5$, CR$^a$R$^b$OR$^5$, CR$^a$R$^b$OC(O)R$^5$, CR$^a$R$^b$OC(O)OR$^5$ or C(O)CHR$^7$NH$_2$;

$R^5$ and $R^6$ are independently H, or selected from the group consisting of substituted or unsubstituted $C_1$-$C_6$alkyl, $C_3$-$C_6$cycloalkyl and $C_3$-$C_6$cycloalkyl$C_1$-$C_3$alkyl;

$R^7$ is H, $C_1$-$C_6$alkyl, $C_3$-$C_6$cycloalkyl and $C_3$-$C_6$cycloalkyl$C_1$-$C_3$alkyl;

wherein $R^a$ and $R^b$ are independently selected from H and methyl;

or a pharmaceutically acceptable salt, stereoisomer, N-oxide or hydrate thereof;

with the provisos that when $R^3$ is a bond, $R^4$ is H, and $R^1$ and $R^2$ are both unsubstituted alkyl, then if $R^1$ is $C_6$-alkyl, $R^2$ has at least two carbon atoms, and when $R^3$ is a bond, $R^4$ is H, and $R^1$ and $R^2$ are both unsubstituted $C_1$-$C_{20}$ alkyl, then $R^1$ has at least 2 more carbon atoms than $R^2$.

2. A compound according to claim 1, wherein $R^1$ is $C_2$-$C_{20}$ alkenyl substituted with up to three substituents independently selected from the group consisting of halo, —$OR^5$, —$C(O)OR^5$, —$C(O)R^5$, —$OC(O)OR^5$, —$NR^5R^6$, —$C(O)NR^5R^6$, —$OC(O)NR^5R^6$, nitro, cyano and azido.

3. A compound according to claim 1, which is racemic at the $R^1$ position.

4. A compound according to claim 1, in which $R^1$ is at least 75% enantiomerically enriched as regards one enantiomer, preferably greater than 90% enantiomerically enriched.

5. A compound according to claim 1, wherein $R^1$ is 1 trans-nonenyl; $R^2$ is selected from ethyl, propyl, butyl, methyl, cyclohexylmethyl, isobutyl and pentyl; $R^3$ is a bond along with the adjacent carbon defining a keto group; and $R^4$ is H.

6. A compound according to claim 1, wherein in $R^2$, any alkyl, alkenyl, alkynyl, cycloalkyl or cycloalkenyl is substituted with up to three substituents independently selected from the group consisting of halo, —$OR^5$, —$C(O)OR^5$, —$C(O)R^5$, —$OC(O)OR^5$, —$NR^5R^6$, —$C(O)NR^5R^6$, —$OC(O)NR^5R^6$, nitro, cyano and azido, and if $R^2$ is cycloalkyl, the group also includes $C_1$-$C_6$alkyl or $C_1$-$C_6$haloalkyl.

7. A compound according to claim 6, wherein $R^2$ is $C_1$-$C_{20}$ alkyl which is substituted or unsubstituted.

8. A compound according to claim 6, wherein $R^2$ is $C_1$-$C_6$ alkyl, including methyl, ethyl, n-propyl, isopropyl, n-butyl, isobutyl, sec-butyl, tert-butyl, n-pentyl and n-hexyl, any of which alkyl species being optionally substituted with 1, 2 or where valance permits 3 substituents independently selected from $C_1$-$C_4$alkyl, $C_1$-$C_4$ haloalkyl, halo, hydroxy, $C_1$-$C_4$alkoxy, $C_1$-$C_4$hydroxyalkyl and $C_1$-$C_4$alkylcarbonyl.

9. A compound according to claim 1, wherein $R^2$ is $C_3$-$C_6$ cycloalkyl$C_1$-$C_3$ alkyl in which any alkyl or cycloalkyl is optionally substituted with up to three substituents independently selected from the group consisting of halo, —$OR^{5'}$—$C(O)OR^5$, —$C(O)R^5$, —$OC(O)OR^5$, —$NR^5R^6$, —$C(O)NR^5R^6$, —$OC(O)NR^5R^6$ nitro, cyano, and azido, and in the case of cycloalkyl, also $C_1$-$C_6$ alkyl or $C_1$-$C_6$ haloalkyl.

10. A compound according to claim 9, wherein $R^2$ is selected from cyclopropylmethyl, cyclobutylmethyl, cyclopentylmethyl and especially cyclohexylmethyl, any of which cycloalkyl species being optionally substituted with 1, 2 or where valance permits 3 substituents independently selected from $C_1$-$C_4$alkyl, $C_1$-$C_4$haloalkyl, halo, hydroxy, $C_1$-$C_4$alkoxy, $C_1$-$C_4$hydroxyalkyl and $C_1$-$C_4$alkylcarbonyl.

11. A compound according to claim 1 wherein, $R^3$ is a bond to the adjacent carbon thereby defining a keto group.

12. A compound according to claim 1, wherein $R^3$ is H, including the corresponding enol with the gamma ketone function on the pyran ring.

13. A compound according to claim 1, wherein $R^3$ is derivatised with a prodrug moiety selected from $C(O)R^5$, $CR^aR^bOR^5$, $CR^aR^bOC(O)R^5$, $CR^aR^bOC(O)OR^5$ and $C(O)CHR^7NH_2$.

14. A compound according to claim 13, wherein:

$R^3$ as $C(O)R^5$ has $R^5$ as methyl, isopropyl, cyclopropyl or tert-butyl, any of which may be optionally fluorinated;

$R^3$ as $CR^aR^bOR^5$, has $R^a$ and $R^b$ as both H or both methyl and $R^5$ is methyl, isopropyl, cyclopropyl or tert-butyl, any of which may be fluorinated;

$R^3$ as $CR^aR^bOC(O)R^5$, has $R^a$ and $R^b$ as both H or both methyl and $R^5$ is methyl, isopropyl, cyclopropyl or tert-butyl, any of which may be optionally fluorinated;

$R^3$ as $CR^aR^bOC(O)OR^5$, has $R^a$ and $R^b$ as both H or both methyl and $R^5$ is methyl, isopropyl, cyclopropyl or tert-butyl, any of which may be optionally fluorinated; or $R^3$ as $C(O)CHR^7NH_2$, especially wherein $R^7$ is the side chain of an L-amino acid such as alanine, valine, leucine or isoleucine.

15. A compound according to claim 1 wherein $R^4$ is H.

16. A compound according to claim 1, wherein $R^4$ is derivatised with a prodrug moiety selected from the group consisting of $C(O)R^5$, $CRaRbOR^5$, $CRaRbOC(O)R^5$, $CRaRbOC(O)OR^5$ and $C(O)CHR^7NH_2$; wherein $R^a$ and $R^b$ are independently selected from H and methyl.

17. A compound according to claim 16, wherein:

$R^3$ as $C(O)R^5$ has $R^5$ as methyl, isopropyl, cyclopropyl or tert-butyl, any of which may be optionally fluorinated;

$R^3$ as $CR^aR^bOR^5$, has $R^a$ and $R^b$ as both H or both methyl and $R^5$ is methyl, isopropyl, cyclopropyl or tert-butyl, any of which may be fluorinated;

$R^3$ as $CR^aR^bOC(O)R_5$, has $R^a$ and $R^b$ as both H or both methyl and $R_5$ is methyl, isopropyl, cyclopropyl or tert-butyl, any of which may be optionally fluorinated;

$R^3$ as $CR^aR^bOC(O)OR_5$, has $R^a$ and $R^b$ as both H or both methyl and $R_5$ is methyl, isopropyl, cyclopropyl or tert-butyl, any of which may be optionally fluorinated; or $R^3$ as $C(O)CHR^7NH_2$, especially wherein $R^7$ is the side chain of an L-amino acid such as alanine, valine, leucine or isoleucine.

18. A compound according to claim 1, wherein in $R^5$ and $R^6$, the $C_1$-$C_6$alkyl or cycloalkyl is substituted with one or more selected from the group consisting of halo, hydroxy, $C_1$-$C_4$alkoxy, $C_1$-$C_4$haloalkyl, hydroxy$C_1$-$C_4$alkyl, $C_1$-$C_4$alkylcarbonyl, SH, SMe, COOH, COO$C_1$-$C_4$alkyl and CONH$_2$.

19. A compound according to claim 1, wherein in $R^7$, the $C_1$-$C_6$alkyl or $C_3$-$C_6$cycloalkyl is substituted with one or more from the group consisting of halo, hydroxy, phenyl, $C_1$-$C_4$alkoxy, $C_1$-$C_4$haloalkyl, hydroxy$C_1$-$C_4$alkyl, $C_1$-$C_4$alkylcarbonyl, SH, SMe, COOH, COO$C_1$-$C_4$alkyl and CONH$_2$.

20. The compound according to claim 1, wherein said compound is (E)-3-butyryl-6-(non-1-en-1-yl)-4-hydroxy-5,6-dihydro-2H-pyran-2-one or a pharmaceutically acceptable salt, stereoisomer, N-oxide or hydrate thereof.

21. A compound according to claim 1, in combination with a pharmaceutically acceptable excipient.

22. A pharmaceutical composition comprising a compound as defined in claim 1 or a pharmaceutically acceptable salt, stereoisomer, N-oxide or hydrate thereof, and a pharmaceutically acceptable carrier, vehicle or diluent therefor.

23. A method for inhibiting bacterial growth in a subject suffering from a bacterial infection, comprising administering a therapeutically effective amount of a compound of Formula I, according to claim 1, or a therapeutically acceptable salt thereof, to the subject.

24. A method for inhibiting bacterial growth in a subject at risk for bacterial colonisation, comprising administering a therapeutically effective amount of a compound of Formula I, according to claim 1, or a therapeutically acceptable salt thereof, to the subject.

25. The method according to claim 23, wherein said bacterial infection is a Gram-positive bacterial infection.

26. The method according to claim 24, wherein said bacterial colonization is a Gram-positive bacterial colonization.

27. A method for inhibiting bacterial growth on skin as a preoperative measure for surgical site infection prevention, comprising administering a therapeutically effective amount of a compound of Formula I according to claim 1, or a therapeutically acceptable salt thereof, to a subject.

28. A pharmaceutical composition comprising a compound according to claim 1, wherein said composition is in a form suitable for nasal application against *Staphylococcus aureus*.

29. A pharmaceutical composition comprising a compound according to claim 1 in combination with mupirocin.

* * * * *